United States Patent [19]
Wand et al.

[11] Patent Number: 5,271,864
[45] Date of Patent: Dec. 21, 1993

[54] FERROELECTRIC LIQUID CRYSTAL COMPOUNDS WITH CYCLOHEXENYL CORES AND COMPOSITIONS CONTAINING THEM

[75] Inventors: Michael D. Wand; Rohini T. Vohra, both of Boulder; Kundalika M. More, Denver; William N. Thurmes, Longmont, all of Colo.

[73] Assignee: Displaytech, Inc., Boulder, Colo.

[21] Appl. No.: 926,503

[22] Filed: Aug. 7, 1992

[51] Int. Cl.$^5$ ................ C09K 19/34; C07D 239/02; C07D 285/12; C07C 69/76

[52] U.S. Cl. .................. 252/299.61; 252/299.67; 544/242; 544/298; 544/335; 548/125; 548/136; 560/59; 560/102; 568/630

[58] Field of Search .......... 252/299.01, 299.61, 252/299.63, 299.67; 544/242, 248, 335; 548/125, 136; 568/630; 560/59, 102; 546/314

[56] References Cited

U.S. PATENT DOCUMENTS 4,943,384  7/1990  Sucrow et al. .......... 252/299.61
5,180,521  1/1993  Eidenschink et al. ...... 252/299.61

FOREIGN PATENT DOCUMENTS 0331091   9/1989  European Pat. Off.
3906040   9/1989  Fed. Rep. of Germany.
8705015   5/1987  PCT Int'l Appl.
89279241/39  6/1989  World Int. Prop. O.

OTHER PUBLICATIONS

Li et al. (1991) Mol. Cryst. Liq. Cryst. 199:379–386.

Fung et al. (1989) Mol. Cryst. Liq. Cryst. Let. 6A(6):1-91–196.
Bezborodov et al. (1989) Liq. Cryst. 4(2):209–215.

Primary Examiner—Robert L. Stoll
Assistant Examiner—Shean C. Wu
Attorney, Agent, or Firm—Greenlee and Winner

[57] ABSTRACT

Ferroelectric liquid crystal compounds and compositions containing cyclohexenyl derivatives are provided. Specifically provided are compounds of formula:

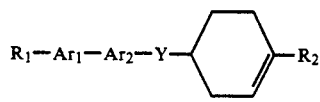

wherein $R_1$ and $R_2$ can be an alkyl, cycloalkyl, alkenyl, alkoxy, thioalkyl, alkylsilyl group having from one to about twenty carbon atoms. Y denotes —COO—, —OOC—, —CH$_2$O—, or —OCH$_2$—; and Ar$_1$ and Ar$_2$, independently of one another, can be selected from the group consisting of phenyl rings, halogenated phenyl rings and nitrogen-containing aromatic groups. In preferred embodiments the compounds of this invention contain at least one nitrogen-containing aromatic ring. Ar$_1$ and Ar$_2$ can be selected from 1,4-phenyl, mono- or dihalogenated 1,4-phenyl, 2,5-pyridinyl, 2,5-pyrimidyl, 2,5-pyrazinyl, 2,5-thiadiazole, 3,6-pyridazinyl and 1,4-cyclohexyl either or both be chiral racemic groups or chiral nonracemic groups.

28 Claims, No Drawings

FERROELECTRIC LIQUID CRYSTAL COMPOUNDS WITH CYCLOHEXENYL CORES AND COMPOSITIONS CONTAINING THEM

This invention was made with partial support of the United States Government under National Science Foundation grant number ISI 90000-40 and U.S. Army Research Office contract number DAAL03-91-C-0051. The United States Government has certain rights in this invention.

FIELD OF THE INVENTION

The present invention relates to liquid crystal compounds which are cyclohexenyl ethers and cyclohexenyl esters which have application in liquid crystal devices, particularly in ferroelectric liquid crystal devices useful in electro-optical and display device applications.

BACKGROUND OF THE INVENTION

Liquid crystals have found use in a variety of electro-optical and display device applications, in particular those which require compact, energy-efficient, voltage-controlled light valves such as watch and calculator displays. Liquid crystal displays have a number of unique useful characteristics, including low voltage and low power of operation. In such displays, a thin layer of liquid crystal material is placed between glass plates and the optical properties of small domains in the layer is controlled by the application of electric fields with high spatial resolution. These devices are based upon the dielectric alignment effects in nematic, cholesteric and smectic phases of the liquid crystal compound in which, by virtue of dielectric anisotropy, the average molecular long axis of the compound takes up a preferred orientation in an applied electric field. However, since the coupling to an applied electric field by this mechanism is rather weak, the electro-optical response time of liquid crystal based displays may be too slow for many potential applications such as in flat-panel displays for use in video terminals, oscilloscopes, radar and television screens. Fast optical response times become increasingly important for applications to larger area display devices. Insufficient nonlinearity of liquid crystal based displays can also impose limitations for many potential applications.

Electro-optic effects with sub-microsecond switching speeds can be achieved using the technology of ferroelectric liquid crystals (FLCs) of N. A. Clark and S. T. Lagerwall1 (1980) Appl. Phys. Lett. 36:899 and U.S. Pat. No. 4,367,924. These investigators have reported display structures prepared using FLC materials having not only high speed response (about 1,000 times faster than currently used twisted nematic devices), but which also exhibit bistable, threshold sensitive switching. Such properties make FLC based devices excellent candidates for light modulation devices including matrix addressed light valves containing a large number of elements for passive displays of graphic and pictorial information, optical processing applications, as well as for high information content dichroic displays.

Smectic C liquid crystal phases composed of chiral, nonracemic molecules possess a spontaneous ferroelectric polarization, or macroscopic dipole moment, deriving from a dissymmetry in the orientation of molecular dipoles in the liquid crystal phases (Meyer et al. (1975) J. Phys. (Les Ulis, Fr) 36:L-69). The ferroelectric polarization density is an intrinsic property of the material making up the phase and has a magnitude and sign for a given material under a given set of conditions. In ferroelectric liquid crystal display devices, like those of Clark and Lagerwall, appropriate application of an external electric field results in alignment of the chiral molecules in the ferroelectric liquid crystal phase with the applied field. When the sign of the applied field is reversed, realignment or switching of the FLC molecules occurs. This switching can be employed for light modulation. Within a large range of electric field strengths, the switching speed (optical rise time) is inversely proportional to applied field strength and polarization or dipole density (P), and directly proportional to orientational viscosity. Fast switching speeds are then associated with FLC phases which possess high polarization density and low orientational viscosity.

A basic requirement for application of ferroelectric liquid crystals in such devices is the availability of chemically stable liquid crystal materials which exhibit ferroelectric phases (chiral smectic C.) over a substantial temperature range about room temperature. Useful device operating temperatures range from about 10° C. to about 80° C. More typical device operating temperatures range from 10° C. to 30° C. In some cases, the ferroelectric liquid crystal compound itself will possess an enantiotropic or monotropic ferroelectric (chiral smectic C*) liquid crystal phase. Ferroelectric liquid crystal mixtures possessing chiral smectic C* phases with useful temperature ranges can also be obtained by admixture of chiral, nonracemic compounds, designated ferroelectric liquid crystal dopants, into a liquid crystal host material (which may or may not be composed of chiral molecules). Addition of the dopant can affect the ferroelectric polarization density and/or the viscosity of the C* phase and thereby affect the switching speed. Desirable FLC dopants are molecules which impart high ferroelectric polarization density to an FLC material without significantly increasing the orientational viscosity of the mixture. The components of FLC mixtures can also be adjusted to vary phase transition temperatures or to introduce desired LC phases.

In addition to the above-described characteristics, the composition of ferroelectric liquid crystal materials can be adjusted to vary the tilt angle, pitch, stability and mixing properties of the FLC materials. Addition of molecules which optimally impart a 22.5° tilt angle to an FLC material used in a shutter or light switch, results in maximum throughout in the "ON" state of the device. A 22.5° tilt angle is particularly desirable for FLC materials used in direct drive, flat panel display applications. A longer helix pitch in the smectic C* phase, particularly a pitch longer than about 3.0 μm, is also a desirable characteristic of FLC materials for certain applications, since such a longer helix pitch improves the alignment of the FLC compounds in electro-optical devices, decreases surface interactions and as a consequence improves the usefulness of these compounds in SSFLC (Surface Stabilized Ferroelectric Liquid Crystal) devices. FLC components can also be added which increase the stability of the smectic phases of the FLC material, for example, by suppressing crystallization of FLC materials, and/or improving the miscibility and-/or viscosity of the liquid crystal composition.

Thermotropic liquid crystal molecules typically possess structures which combine a rigid core coupled with two relatively "floppy" tails (see Demus et al. (1974) Flussige Kristalle In Tabellen, VEB Deutscher Verlag fur Grundstoffindustrie, Lebzig for a compilation of the molecular structures of LC molecules). FLC materials have been prepared by the introduction of a stereocenter into one of the tails, thus introducing chirality. The first FLC compound to be characterized was DO-BAMBC (Meyer et al., supra) which contains an (S)-2-methylbutyloxy chiral tail. Pure DOBAMBC exhibits a smectic C* phase with a ferroelectric polarization of $-3$ nC/cm$^2$.

There are a number of reports of compounds containing two or more aromatic rings such as those having phenylbenzoate, biphenyl, phenylpyrimidine, phenylpyridine and related cores coupled to chiral tail units which possess smectic C* phases displaying fast switching speeds at room temperature, or which can be employed as FLC dopants to induce high polarization and fast switching speeds when combined in mixtures with FLC host materials. There are also several reports of FLC compounds having cores which contain cyclohexane and cyclohexene rings.

The following are exemplary reports of FLC compounds containing cyclohexane or cyclohexene rings:

Li et al. (1991) Mol. Cryst. Liq. Cryst. 199:379–386 disclose cyclohexenyl liquid crystal compounds, having a chiral center in the mesogenic core, derived from the Diels-Alder reaction between myrcene and methyl acrylate, followed by hydrolysis and esterification with 4-hydroxy-4'-n-alkoxybiphenyl. The liquid crystal materials reported have the following structure:

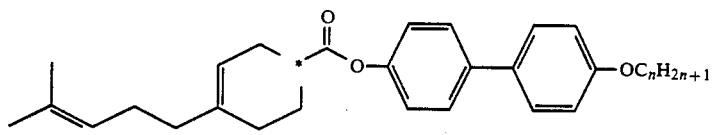

The lower member cyclohexenecarboxylates (n = 1 and 2) have a large nematic range, and the higher members (n=3–10) have multiple smectic phases in addition to the nematic phase. The presence of the cyclohexene ring is suggested to lead to multiple smectic phases. Nonracemic 4'-n-octyloxybiphenyl 4-(4-methyl-3-pentenyl)-3-cyclohexenecarboxylate is reported to have a smectic C phase and a normal tilt angle, however, its polarization density is extremely small (extrapolated polarization density, $P_{ext}$, less than 1 nC/cm$^2$). It is suggested that the small polarization density is due to the small dipole associated with the chiral carbon in the tilt plane, which does not contribute to P. Further, the carbonyl adjacent to the chiral produces nearly equivalent, but opposite, dipole moments in the two potential configurations, which occur with nearly equal probability.

Fung et al. (1989) Mol. Cryst. Liq. Cryst. Let. 6(6):191–196 report liquid crystal compounds containing a cyclohexene ring, derived from the Diels-Alder reaction between mycrene and methyl acrylate, followed by hydrolysis and esterification of the resulting acid with 4-hydroxy-4'-methoxybiphenyl or 4-hydroxy-4'-cyanobiphenyl. The liquid crystal materials reported have the following structure:

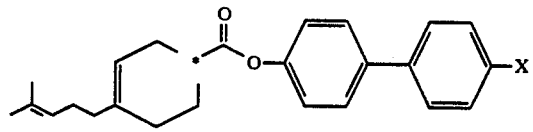

where X is a methoxy or cyano group. The two compounds exhibit broad nematic ranges (79–153° C. and 93–152° C., respectively).

Bezborodov et al. (1989) Liq. Cryst. 4(2):209–215 disclose the mesomorphic (nematic) properties of cyclohexenyl liquid crystal compounds derived from 4-substituted phenols and 4-n-alkylcyclohexene-1-carbonyl chlorides where the double bond is in the 1, 2 or 3 position in the cyclohexene ring. The reference indicates that compounds containing the double bond in the 2 position of the cyclohexene (numbering from the carboxy group as is conventional) are the most promising for use as liquid crystal components, since the appearance of the double bond in the first or 3 positions of the ring causes a large distortion in the shape of the molecule. This distortion reportedly affects both the mesophase (nematic) range and the melting point.

German patent document, Reiffenrath et al., DE 3906040, published Sep. 21, 1989 and WPI Abstract 89-279241/39, refers to cyclohexene derivatives having the general formula:

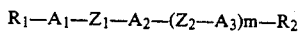

where $R_1$ and $R_2$ are 1–15 carbon alkyl or 3–15 carbon alkenyl groups, optionally with one CN or at least one flourine or chlorine substituent, in which a CH$_2$ group can be replaced with —O—, —OCO—, —COO— or —OCOO—, and one of $R_1$ and $R_2$ can be CN; where $A_1$, $A_2$ and $A_3$ can be 1,4-cyclohexenylene or trans-1,4-cyclohexylene in which one or two non-adjacent CH$_2$ groups can be replaced by —O—, or 1,4-phenylene, optionally with one or two fluorine substituents, in which one or two CH$_2$ groups can be replaced by nitrogen, at least one of $A_{1-3}$ being 2,3-difluoro-1,4-phenylene, and at least one of $A_{1-3}$ being 1,4-cyclohexenylene; and where $Z_1$ and $Z_2$ can be —COO—, —OCO—, —CH$_2$O—, —OCH$_2$—, —CH$_2$CH$_2$— or a single bond. The reference refers to 1,4-cyclohexenylenes having the double bond in the 1, 2 or 3 position.

Tanaka et al. (1989) European Patent Application, Pub. No. 331091 refers to tetracyclic cyclohexylcyclohexene derivatives having the formula:

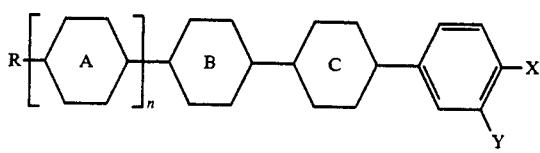

where R is a straight-chained alkyl group having 1–9 carbon atoms; A is a cyclohexyl, cyclohexenyl, or phenyl ring; B and C are cyclohexyl or clycohexenyl rings; n is 0 or 1; when n is 0, X is a cyano group and Y is a hydrogen or fluorine atom; when n is 1, X is a fluorine atom, a straight-chained alkyl group having 1-9 carbon atoms, and Y is a hydrogen or fluorine atom. The disclosed liquid crystal compounds exhibit high N-I and low C-N or S-N points.

Eidenschink et al., WO 87/05015, discloses cyclohexane containing liquid crystal and ferroelectric liquid crystal compositions having the general formulas:

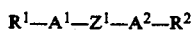

where $A_1$ and $A_2$ can be a phenyl, cyclohexyl, phenylpyrimidine, or substituted cyclohexene ring. Eidenschink et al. does not specifically disclose a cyclohexene ring, but generically discusses reduced groups at page 14, fourth paragraph, and suggests that the claimed compounds can include reduced groups.

While a number of useful liquid crystal and smectic liquid crystal materials (both pure compounds and mixtures) have been reported, there is a growing need for LC and FLC materials with varying properties of pitch and tilt angle for use in varied applications. In order to obtain faster switching speeds, FLC materials with low orientational viscosity are desirable. Further, there is a need for LC host materials and FLC dopants with varying mixing properties (which are dependent, at least in part, on chemical composition) for use in the preparation of FLC mixtures having desired chiral smectic phases at useful device operating temperatures (e.g. about 0°-100° C., preferably around room temperature about 10°-35° C). LC and FLC materials which result in mixtures that are stable to crystallization over useful device operating temperatures are desirable. LC host materials and FLC dopants which are readily synthesized and which impart longer chiral smectic phase pitch, tilt angle of about 22.5°, lower orientational viscosity, broader LC and FLC phases, and suppress crystallization in such mixtures are of particular interest.

SUMMARY OF THE INVENTION

An object of the present invention is to provide new classes of LC and FLC compounds, having core groups containing a cyclohexene ring, which impart improved properties to LC and FLC materials.

The present invention provides cyclohexenyl ether or esters of the formula:

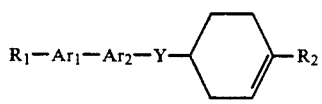

wherein $R_1$ and $R_2$, independently of one another, can be an alkyl, cycloalkyl, alkenyl, alkoxy, ether, thioalkoxyl, thioether or alkylsilyl group having from 1 to about 20 carbon atoms, Y denotes —COO—, —OOC—, —CH$_2$O—, or —OCH$_2$—; and $Ar_1$ and $Ar_2$, independently of one another, can be cyclohexyl rings, phenyl rings or aromatic rings containing one or two nitrogens, for example, a pyridine, a pyrimidine, a pyrazine, a pyridizine, or a thiadiazole. In preferred embodiments, at least one ring $Ar_1$ or $Ar_2$ must be a nitrogen-containing aromatic ring. The non-cyclohexenyl rings can also be mono- or di-halogenated, wherein the halogen is preferably fluorine. Preferred cores contain rings linked in para, linear arrangement.

In general, suitable liquid crystal cores are rigid, linear moieties. Preferred cores are those that are chemically stable and which do not impart high orientational viscosity in the liquid crystal phase. Cores of the present invention have a cyclohexenyl ring and at least one nitrogen-containing aromatic ring. The cyclohexenyl ring can be linked to the other rings of the core through an ester or ether linkage, e.g., —COO—, —OOC—, —CH$_2$O—, or —OCH$_2$—. The non-cyclohexenyl rings of the core include, but are not limited to, 1,4-phenyl, mono- or dihalogenated 1,4-phenyl, 2,5-pyridinyl, 2,5-pyrimidyl, 2,5-pyrazinyl, 2,5-thiadiazole, and 3,6-pyridazinyl.

Exemplary, $Ar_1$ and $Ar_2$ rings can include, but are not limited to, the following:

1,4-substituted phenyl ring, e.g.,: 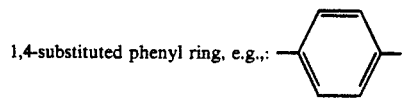

Mono- or di-fluorinated phenyl ring, e.g.,: 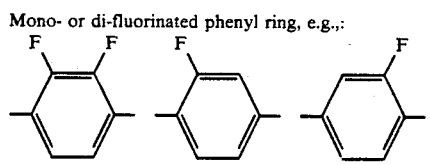

2,5-substituted pyridine ring, e.g.,: 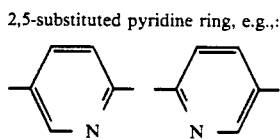

2,5-substituted pyrimidine rings, e.g.,: 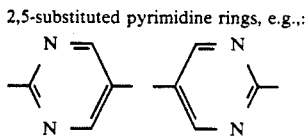

2,5-substituted pyrazine ring, e.g.,: 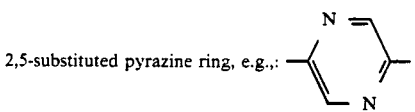

2,5-substituted thiadiazole ring, e.g.,: 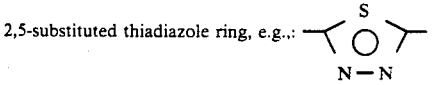

3,6-substituted pyridizine ring, e.g.,: 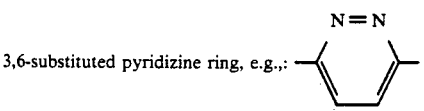

1,4-cyclohexyl ring, e.g.,: 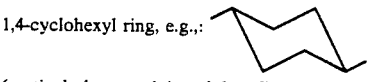

(particularly trans-1,4-cyclohexyl)

Preferred nitrogen-containing $Ar_1$ and $Ar_2$ moieties of this invention are 2,5-substituted pyrimidine or 2,5-substituted pyridine rings. Preferred halogenated Ar and $Ar_2$ are fluorinated 1,4-phenyl rings and fluorinated pyridine rings with 2-fluoro-, 3-fluoro- or 2,3-difluoro-substituted 1,4-phenyl rings and 2-fluoro-3,6-substituted pyridine rings being more preferred. More preferred cores are those containing a 1,4-phenyl ring or fluorinated 1,4-phenyl ring in combination with a 2,5-substituted pyrimidine or 2,5-substituted pyridine ring.

The tail units $R_1$ and $R_2$ are preferably linked on opposite ends of the core in a para arrangement. The non-cyclohexenyl rings of the core can be arranged within the core in either orientation with respect to the cyclohexenyl and $R_1$ tail unit.

The compounds of the present invention have $R_1$ which may or may not be chiral. R tails of the present invention include alkyl, alkenyl, alkoxy, thioalkyl, thioether, alkylsilyl or cycloalkyl groups having one to twenty carbon atoms. The $R_1$ tail units can be straight-chain or branched. Alkenyl $R_1$ tails preferably have one double bond and more preferably have an $\omega$-double bond. $R_1$ tails include alkoxy tails, e.g., $R_1=C_nH_{2n+1}-O-$ (where n is preferably 20 or less) and ether tails, e.g., $C_nH_{2n+1}-O-CH_2$ (where n is preferably 19 or less) and preferably contain one oxygen atom. $R_1$ tails include thioalkyl tails, e.g., $R_1=C_nH_{2n+1}-S-$ (where n is preferably 20 or less), and thioether tails, e.g., $R_1=C_nH_{2n+1}-S-CH_2$ (where n is preferably less than 19), and preferably contain one sulfur atom. $R_1$ tails also include alkylsilyl tails, e.g., $C_nH_{2n+1}-Si(CH_3)_2-C_mH_{2m+1}-$ (where n+m is preferably 18 or less) or $(CH_3)_3Si-C_nH_{2n+1}-$ (where n is preferably 17 or less), where a dialkylsilyl group such as $(CH_3)_2Si$ is inserted within an alkyl chain. $R_1$ cycloalkyl tails include cyclopropyl tails, particularly wherein a cyclopropyl group is at the end of the tail ($\omega$-position), e.g., c—propyl—$C_nH_{2n+1}$— (where n is preferably 17 or less). Preferred $R_1$ tails have one to twenty carbon atoms, i.e., $n \leq 20$ in the above exemplified formulas. $R_1$ tails of the present invention are most preferably alkyl, alkoxy and $\omega$-alkenyl tails containing one to twenty carbon atoms. Non-adjacent carbon atoms in $R_1$ alkyl, alkoxy or alkenyl tails can be replaced with a double bond, oxygen atom, sulfur atom, cyclopropyl group or silylalkyl group such as $Si(CH_3)_2$. Preferred tails contain only one such substitution. $R_1$ tails more preferably contain three to twelve carbon atoms and most preferably five to twelve carbon atoms.

In general, $R_2$ can be any of the alkyl, alkenyl, alkoxy, ether, cycloalkyl, thioalkyl, thioether and alkylsilyl groups defined above for $R_1$. $R_1$ and $R_2$ can be the same or different tail groups. Since $R_2$ is attached to the cyclohexene ring at the double bond, preferred $R_2$ tails have a CH2 group at the first position in the tail. As with $R_1$, $R_2$ tails can be straight-chain or branched, chiral nonracemic or achiral groups. Preferred $R_2$ tails contain 1 to 20 carbon atoms. Tails having three to twelve carbons are more preferred and tails having five to twelve carbons are most preferred.

$R_2$ that are alkyl and alkenyl groups are more preferred. For $R_2$ that is alkenyl, $\omega$-alkenyl groups are preferred. For $R_2$ that is a thioether or ether, tails containing a single S or O are preferred, such as $C_nH_{2n+1}-S-CH_2-$ and $C_nH_{2n+1}-O-CH_2-$ (where n is preferably 19 or less). In alkyl, alkenyl, thioether and ether $R_2$ tails, one or more of the non-neighboring carbon atoms can be replaced with a cyclopropyl group, alkylsilyl group, S atom or O atom. Preferably, $R_2$ groups contain only one such substitution and such substitution is preferably not at the 1-position in the tail.

If $R_2$ or $R_1$ is an alkenyl group, the double bonds can be located at any position in the segment and can be cis or trans substituted double bonds. However, trans double bonds are preferred over cis double bonds which are likely to result in reduced solubility of the compound in host materials. Additionally, cis double bonds in $R_1$ and $R_2$ tails will likely narrow the smectic C* range.

$R_1$ and $R_2$ can be straight chain or branched. Branching of $R_1$ and/or $R_2$ can broaden the smectic C* phase of the compound itself or of an FLC mixture containing the compound. The branching effect is enhanced when branching is more distant from the core. It has also been observed that if branching occurs at carbons 2-8 (relative to the core), the polarization density of the FLC molecule is generally not significantly affected.

Specific $R_1$ and/or $R_2$ groups include, but are not limited to: methyl, ethyl, n-propyl, iso-propyl, n-butyl, s-butyl, isobutyl, t-butyl, n-pentyl, 1-methylbutyl, 2-methylbutyl, 3-methylbutyl, 2,2-dimethylpropyl, 1,1-dimethylpropyl, n-hexyl, 1-methylpentyl, 2-methylpentyl, 3-methylpentyl, 4-methylpentyl, n-heptyl, 1-methylhexyl, 2-methylhexyl, 3-methylhexyl, 4-methylhexyl, 5-methylhexyl, n-octyl, 1-methylheptyl, 2-methylheptyl, 3-methylheptyl, 4-methylheptyl, 5-methylheptyl, 6-methylheptyl, n-nonyl, 1-methyloctyl, 2-methyloctyl, 3-methyloctyl, 4-methyloctyl, 5-methyloctyl, 6-methyloctyl, 7-methyloctyl, n-decyl, 1-methylnonyl, 2-methylnonyl, 3-methylnonyl, 4-methylnonyl, 5-methylnonyl, 6-methylnonyl, 7-methylnonyl, 8-methylnonyl, dimethylpentyl, dimethylhexyl, dimethylheptyl, dimethyloctyl, dimethylnonyl, n-undecyl, n-dodecyl, dimethyldecyl, n-propadecyl, n-butadecyl, n-pentadecyl, n-hexadecyl, n-heptadecyl, n-octadecyl, 3-butenyl, 4-pentenyl, 5-hexenyl, 6-heptenyl, n-propoxy, n-ethoxy, n-butoxy, n-undecoxy, n-dodecoxy, 2-methoxymethyl, 2-methoxypentyl, 2-oxypentyl, 3-oxypentyl, 4-oxypentyl, 2-oxyhexyl, 3-oxyhexyl, 4-oxyhexyl, 5-oxyhexyl, 2-oxyheptyl, 3-oxyheptyl, 4-oxyheptyl, 5-oxyheptyl and 6-oxyheptyl, n-5-hexenyl, n-6-heptenyl, n-7-octenyl, n-8-nonenyl, n-9-decenyl, 4-methyl-3-pentenyl, 5-methyl-4-hexenyl, n-8-cyclopropyloctyl, n-7-cyclopropylheptyl, 6-trimethylsilylhexyl, 7-trimethylsilylheptyl, 8-trimethylsilyloctyl, n-butyldimethylsilylbutyl.

Formulas for $R_1$ and/or $R_2$ groups include, but are not limited to the following (where $n \leq 20$):

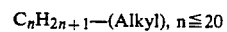

$C_nH_{2n+1}$—(Alkyl), $n \leq 20$

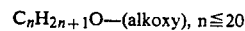

$C_nH_{2n+1}O$—(alkoxy), $n \leq 20$ $C_nH_{2n+1}2$—(thioalkyl), $n \leq 20$

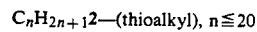

$CH_2=CH-C_nH_{2n+1}$—(alkene), $n \leq 18$

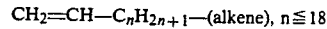

c—propyl—$C_nH_{2n+1}$—(cyclopropylalkyl), $n \leq 17$

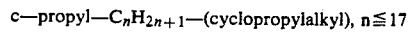

$C_nH_{2n+1}-O-CH_2$—(ether), $n \leq 19$

$C_nH_{2n+1}-S-CH_2$—(thioether), $n \leq 19$

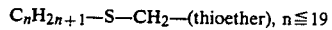

$(CH_3)_3-Si-C_nH_{2n+1}$—(trimethylsilylalkyl), $n \leq 17$

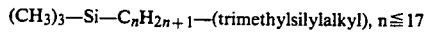

In one aspect, this invention provides cyclohexenyl ethers of the formula:

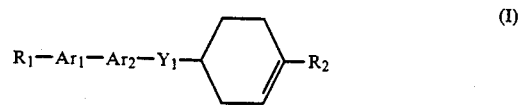

(I)

wherein $R_1$, $R_2$, $Ar_1$ and $Ar_2$ are as defined above and $Y_1$ is —CH$_2$O— or —O—CH$_2$— and wherein at least one of $Ar_1$ or $Ar_2$ is an nitrogen containing aromatic ring.

In a related aspect of this invention compounds of formula I and II having one of $Ar_1$ or $Ar_2$ that is a trans-1,4-cyclohexyl and the other of $Ar_1$ or $Ar_2$ that is a 1,4-phenyl ring are provided which are useful as components of LC and FLC mixtures.

In a second aspect, this invention specifically provides cyclohexenyl esters of the formula:

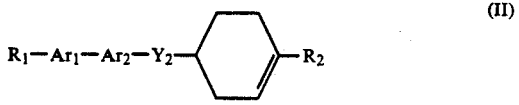

(II)

wherein $R_1$, $R_2$, $Ar_1$ and $Ar_2$ are as defined above and $Y_2$ is —COO— and —OOC—, and wherein at least one of $Ar_1$ or $Ar_2$ is a nitrogen-containing aromatic ring.

In general, the cyclohexenyl ethers and cyclohexenyl esters of the present invention are useful as components of liquid crystal materials. In particular, the cyclohexenyl compounds of this invention can be employed as components of FLC host materials. Chirally asymmetric molecules ($R_1$ and/or $R_2$=chiral nonracemic group) of this invention are also useful as components of FLC materials. Certain of these compounds can impart fast switching speeds to low polarization materials when mixed with such materials to form FLC compositions. Certain of the compounds of this invention can import longer helix pitch to FLC compositions. Certain of the compounds of this invention exhibit liquid crystal phases, including smectic C phases.

This invention includes LC and FLC compositions and FLC host compositions, particularly those compositions with smectic C* helix pitch of 3.0 μm or more, containing one or more of the compounds of formulas I and II.

DETAILED DESCRIPTION OF THE INVENTION

An important feature of the present invention is the finding that the cyclohexenyl ether compounds of formula I and the cyclohexenyl ester compounds of formula II exhibit a longer helix pitch in the smectic C* phase relative to those of analogous compounds having a cyclohexyl ring in the core (Table 1). The magnitude of the pitch of the helix is the distance along the helix axis for one full turn of the helix. The term "pitch" as used herein refers to the magnitude of the pitch. As will be appreciated by those skilled in the art, the longer helix pitch improves the alignment of the FLC compounds and decreases surface interactions in SSFLC electro-optical devices, thus enhancing the usefulness of these compounds in such devices. Alignment is significantly improved and surface interactions are significantly decreased when the helix pitch in the chiral smectic phase is longer than about 3.0 μm.

Another surprising finding of the present invention is that the cyclohexenyl ether and cyclohexenyl ester compounds formulas I and II of the present invention impart a lower tilt angle approaching 22.5° to FLC mixtures than analogous compounds having a cyclohexyl ring. The tilt angle of mixtures containing cyclohexenyl compounds are found to approach 22.5°, the optimal tilt angle for FLC materials in order to obtain maximum contrast used in direct drive, flat panel display applications. Maximum contrast in an SSFLC device is obtained when the voltage step applied across the aligned FLC layer in the cell rotates the optic axis of the cell by a total of 45° between the "OFF" and "ON" states. Contrast depends on the amount of light leaking through in the OFF state and the maximum transmission in the ON state. As illustrated in Table 2, substitution of a cyclohexenyl component for the analogous cyclohexyl component (in a phenylpyrimidine-based host material containing the same FLC dopant) reduces the tilt angle of the FLC material to around 22.5°, the optimal tilt angle.

A further unexpected finding is that the cyclohexenyl compounds of the present invention have improved mixing properties in FLC materials, as compared to their cyclohexyl counterparts. The cyclohexenyl ethers and esters are found to suppress crystallization of FLC materials, thus improving the miscibility and viscosity of the liquid crystal composition. As shown in Table 2, substitution of a cyclohexenyl dopant for the analogous cyclohexyl compound (in phenylpyrimidine host material) reduces both the melting and supercooling points of the phenylpyrimidine material, thereby lowering the temperature at which crystallization occurs and widening the useful C* range.

Yet another unexpected finding is that the cyclohexenyl compounds of the present invention impart faster switching speeds to FLC mixtures, as compared to their cyclohexyl counterparts. Since the switching speed (optical rise time) is directly proportional to orientational viscosity, fast switching speeds are associated with FLC phases possessing low orientational viscosity. Table 2 shows that replacing a cyclohexyl with a cyclohexenyl component (in phenylpyrimidine host material) significantly reduces the rise time of the phenylpyrimidine mixture. This is believed to be a consequence of a lowering of the orientational viscosity of the FLC mixture when the cyclohexenyl component is added.

Table 1 provides phase diagrams for representative cyclohexenyl compounds of this invention. Table 3 provides phase diagrams for representative FLC mixtures of this invention. The cyclohexenyl component used is identified by a formula number and the structure of these components is given below. FLC mixtures comprising the cyclohexenyl compounds of the present invention are found to exhibit smectic C* phases over a broader temperature range than FLC mixtures containing analogous cyclohexyl compounds. Table 3 shows that substitution of a cyclohexenyl component (in phenylpyrimidine host material) for the corresponding cyclohexyl compound can improve the lower range of the C* phase, thereby broadening the useful temperature range of the FLC mixture.

The ease of synthesis of the cyclohexenyl compounds, as compared to their cyclohexyl counterparts, represents yet another advantage of the present invention. More specifically, the synthesis of $R_2$-substituted cyclohexenes via the Diels-Alder reaction (Schemes I and II below) results in a single 1,4-substituted product: the "twist-boat" cyclohexene. In contrast, the synthesis of $R_2$-substituted cyclohexanes results in formation of two isomeric (cis and trans) products which can be more difficult to separate thus making the synthesis of the pure isomers more difficult.

The general synthesis of chiral and achiral compounds of formula I with $Y_1$ equal to —OCH$_2$— and II with $Y_2$= to —OOC— is illustrated in Scheme I, paths A and B, respectively. The general synthesis of chiral and achiral compounds of formula I with $Y_1$ equal to —CH$_2$O— and II with Y$_2$= to —COO— is illustrated in Scheme II, paths A and B, respectively.

In general terms, as shown in Scheme I, compounds of formulas I and II are derived from the Diels-Alder reaction between a substituted diene (1) and ethyl acrylate, followed by hydrolysis of the resulting cyclohexene carboxylic acid ethyl ester (2) to the corresponding acid (3). In path A, acid (3) is reduced to the corresponding cylohexenyl alcohol (4), tosylated (5) and coupled to a substituted cyclohexanol or substituted aryl alcohol (6) to produce the cyclohexenyl ethers (I, Y$_1$=—OCH$_2$—). In path B, acid (3) is transformed into the acid chloride (7) which is then coupled to a substituted cyclohexanol or substituted aryl alcohol (6) to produce the cyclohexene carboxylic acid ester (II, Y$_2$=—OOC—).

In general terms, as shown in Scheme II, compounds of formulas I, where Y is —CH$_2$O—, and II, where Y$_2$ is —COO— are derived from the Diels-Alder reaction between a substituted diene (1) and vinyl acetate, followed by hydrolysis of the resulting acetic acid cylohexenyl ester (8) to the corresponding cyclohexenyl alcohol (9). In path A of Scheme II, alcohol (9) is coupled with an aryl or cyclohexane substituted tosylate (10) to produce the cyclohexenyl ethers (I, Y$_1$=—CH$_2$O—). In path B, alcohol (9) is coupled with the aryl or cyclohexane carboxylic acid chloride (11) to produce the cyclohexenyl ester (II, Y$_2$=—COO—).

The synthetic routes of Schemes I and II can be employed with R$_1$ and R$_2$ which are chiral or achiral and which are straight chain or branched groups. The methods can be readily adapted by those of ordinary skill in the art to the synthesis of compounds of formulas I and II with any of the cores or tail groups described above.

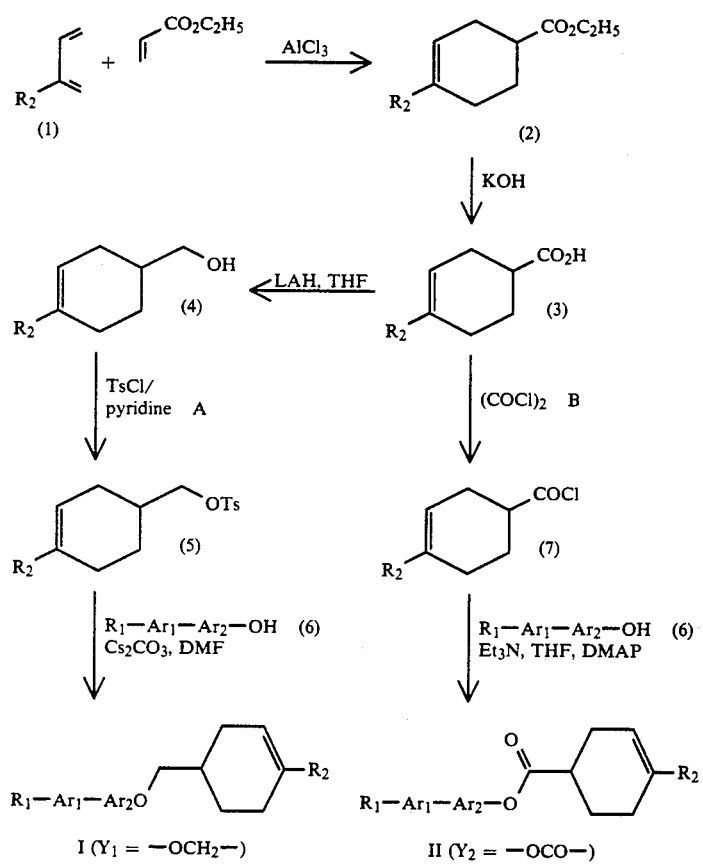

SCHEME I

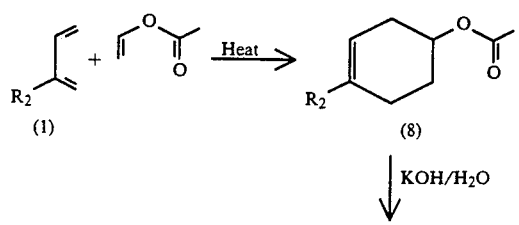

SCHEME II

SCHEME II

-continued

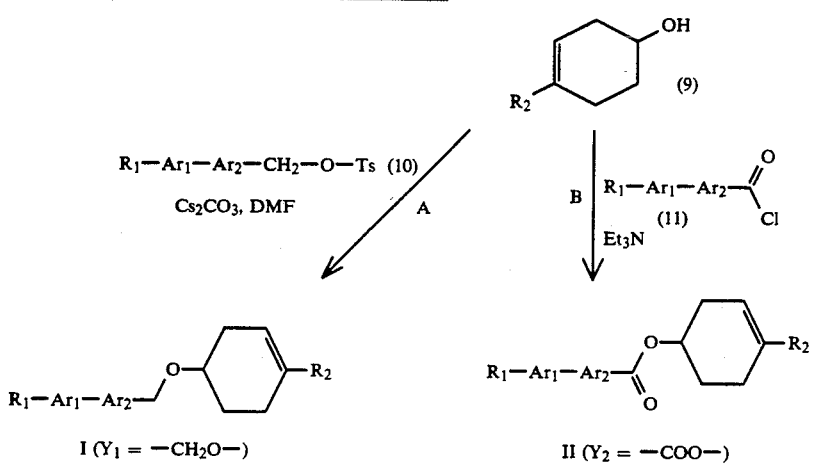

I (Y₁ = —CH₂O—)   II (Y₂ = —COO—)

The starting diene (1) is available commercially or can be synthesized by a variety of methods known in the art. For example, the diene (1A) where R alkyl or alkenyl can be synthesized by reaction of α-bromomethylbutadiene (from bromination of isoprene with n-bromosuccinimide (NBS)) with an appropriate Gringard reagent:

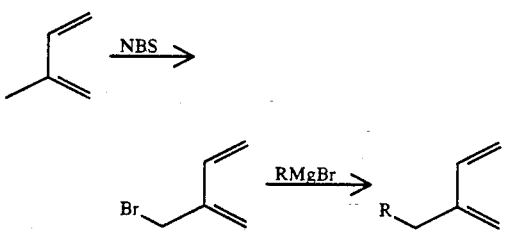

(1A)

Alternatively, the starting diene (1) where R₂ is alkoxy, can be synthesized, for example, by reaction of α-bromomethyl butadiene with sodium n-butoxide, for example, in THF.

The procedure illustrated in Schemes I and II can be used or readily adopted by known variants to prepare cyclohexenyl ethers and esters of this invention.

The substituted cyclohexanols or substituted aryl alcohols (e.g., 6, 10) employed for the preparation of the compounds of formulas I and II are either commercially available or can be prepared by methods known to the art. Carboxylic acid starting materials and their corresponding acid chlorides (11) are also readily available. Descriptions in the examples and Schemes I and II provide guidance for the synthesis of compounds having selected Ar₁ and Ar₂ core units and selected R₁ and R₂ groups.

Thiadiazoles of the structure:

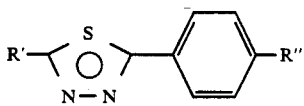

where R' and/or R" is an alkyl, alkenyl, alkoxy, thioalkyl, silylalkyl, or cyclopropyl group, can be synthesized, for example, as described in published European patent application 89105489.2, or by routine adaptation of those methods. Achiral and chiral nonracemic tails can be attached to the thiadiazole ring by conventional methods. Means for coupling the thiazole ring to other rings in the cores of this invention are known in the art.

Alkyl, alkenyl, alkoxy, ether, thioalkyl, thioether, alkylsilyl, and cycloalkyl R₁ and R₂ groups can be readily introduced by routine adaptation of known methods into the cyclohexenyl cores of the present invention in view of the teachings herein.

Dialkylsilyl groups can be introduced into R₁ or R₂ tails employing known methods, for example as described in EP application Ser. No. 355,008 published Feb. 21, 1990, or by routine adaptation of methods described therein.

R₂— and R₁-substituted starting materials are commercially available or can be readily synthesized by known methods or routine adaptation of known methods particularly in view of the guidance provided herein.

Preferred examples of the compounds of this invention include but are not limited to:

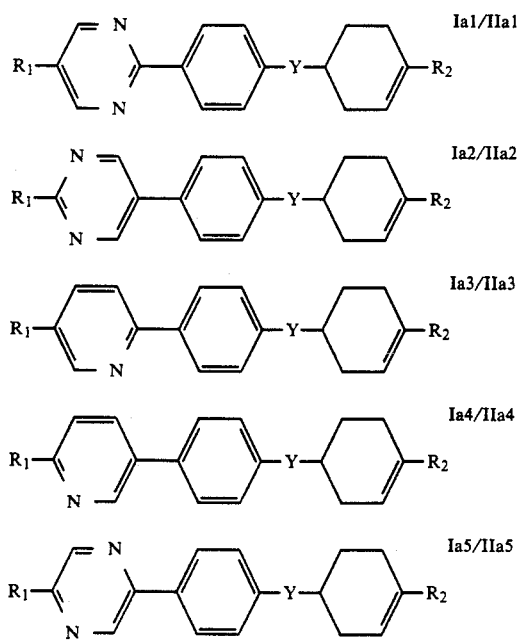

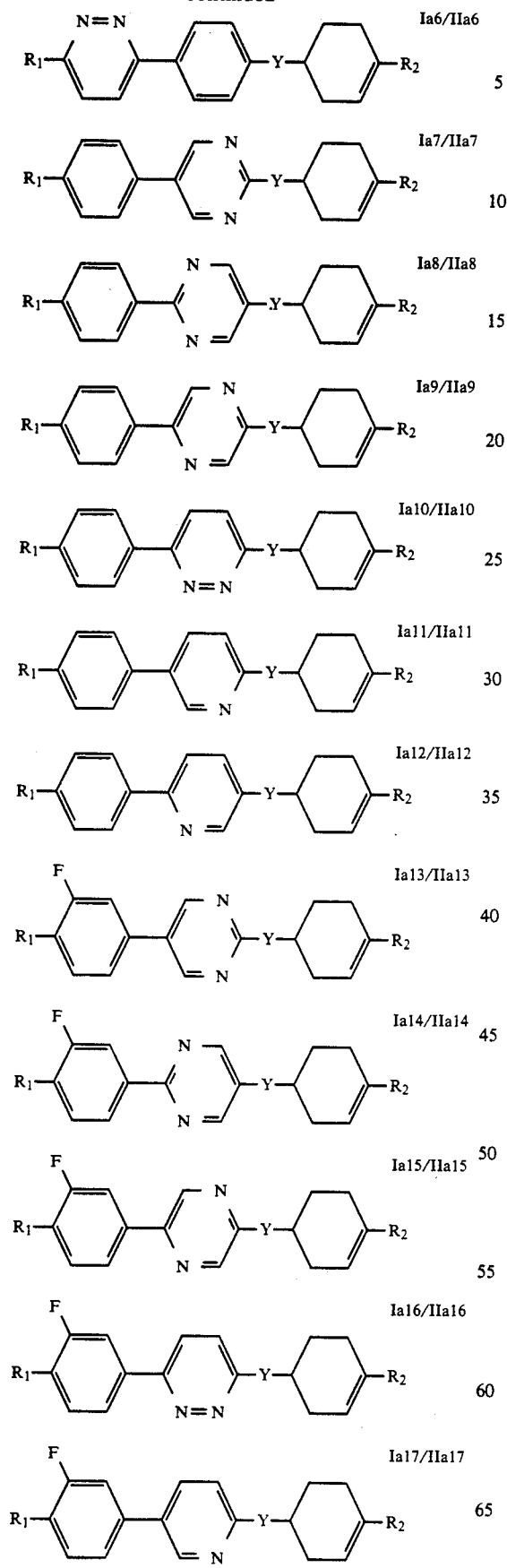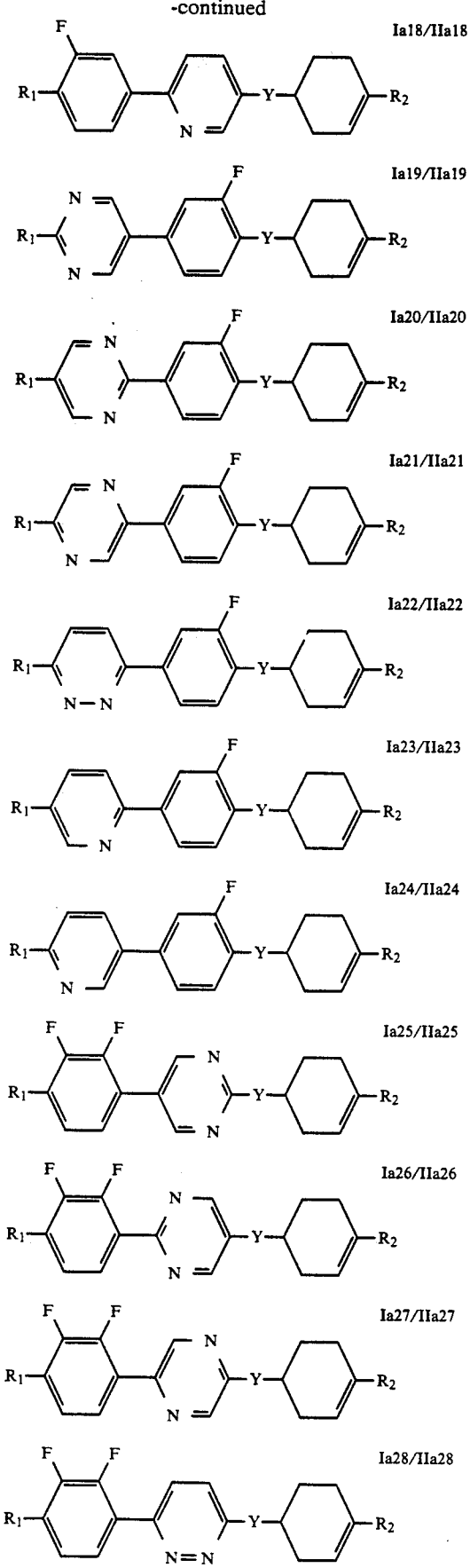

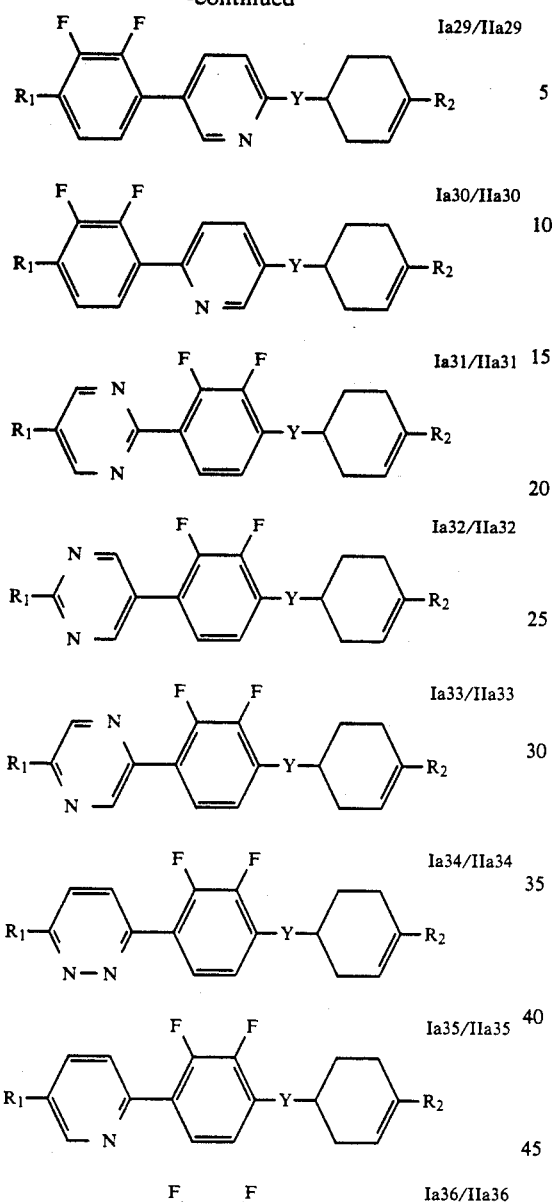
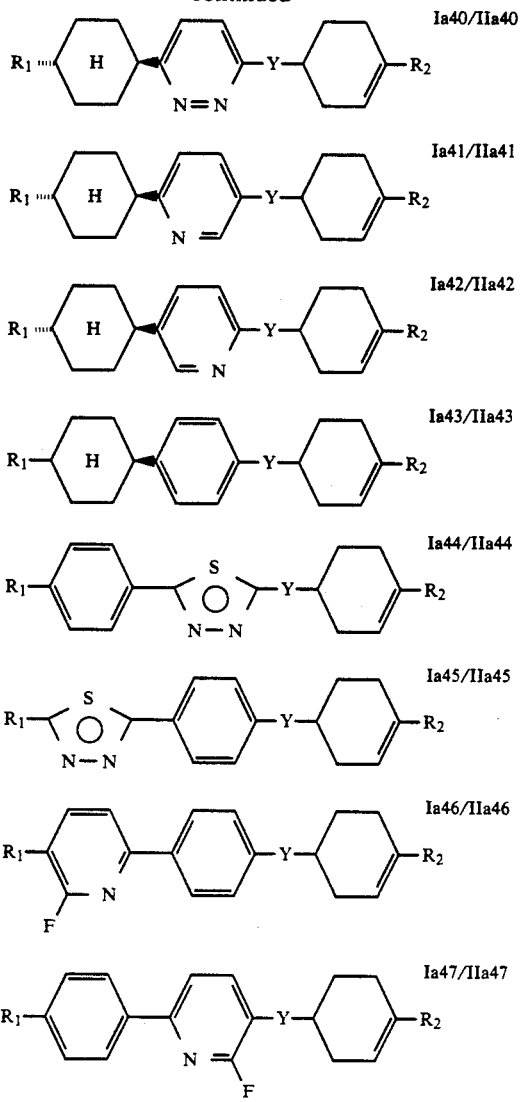
More specific preferred examples of compounds of this invention include but are not limited to:
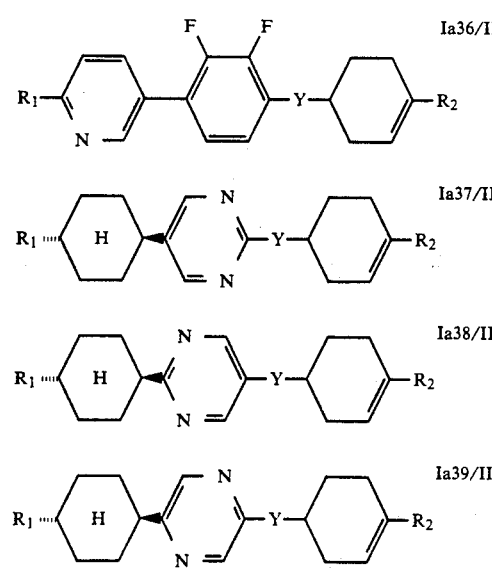

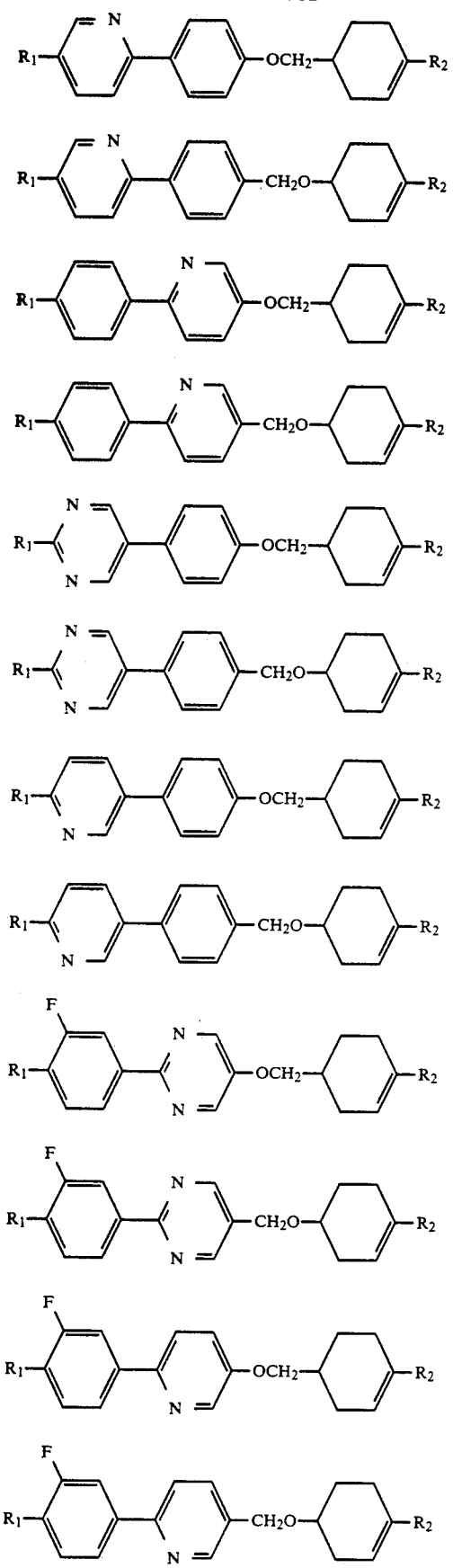
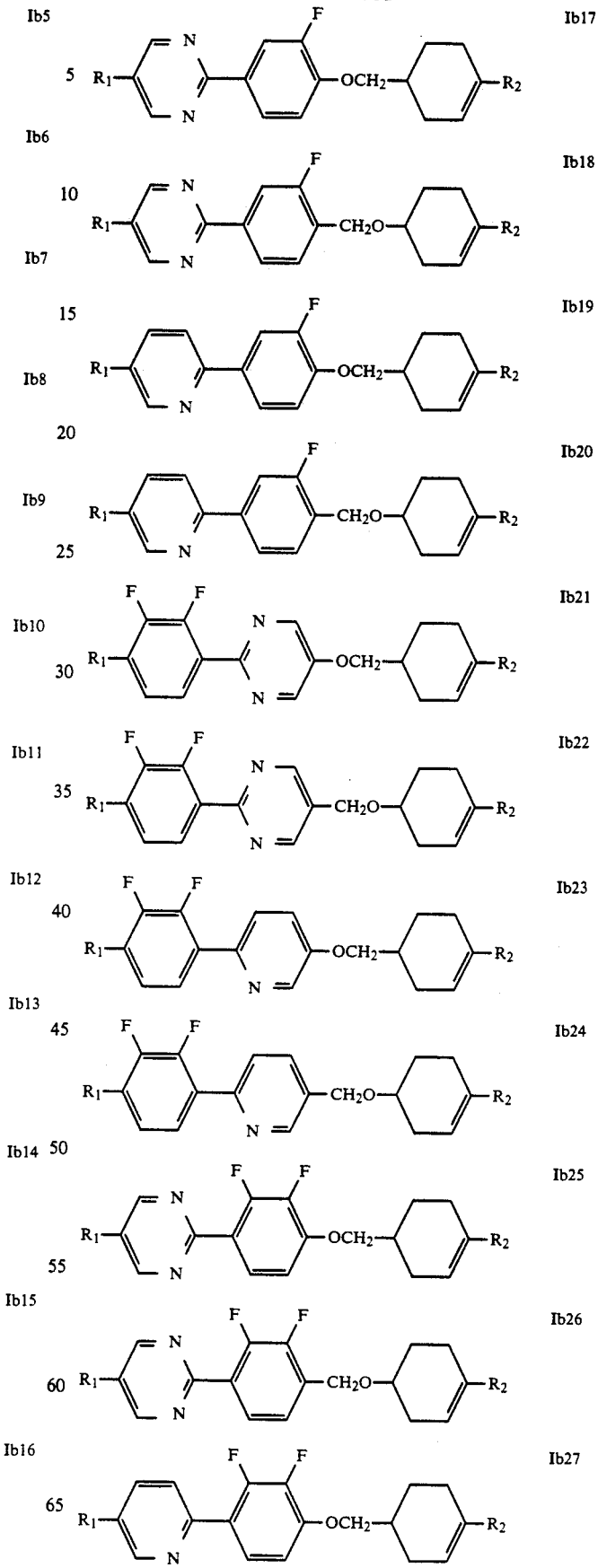

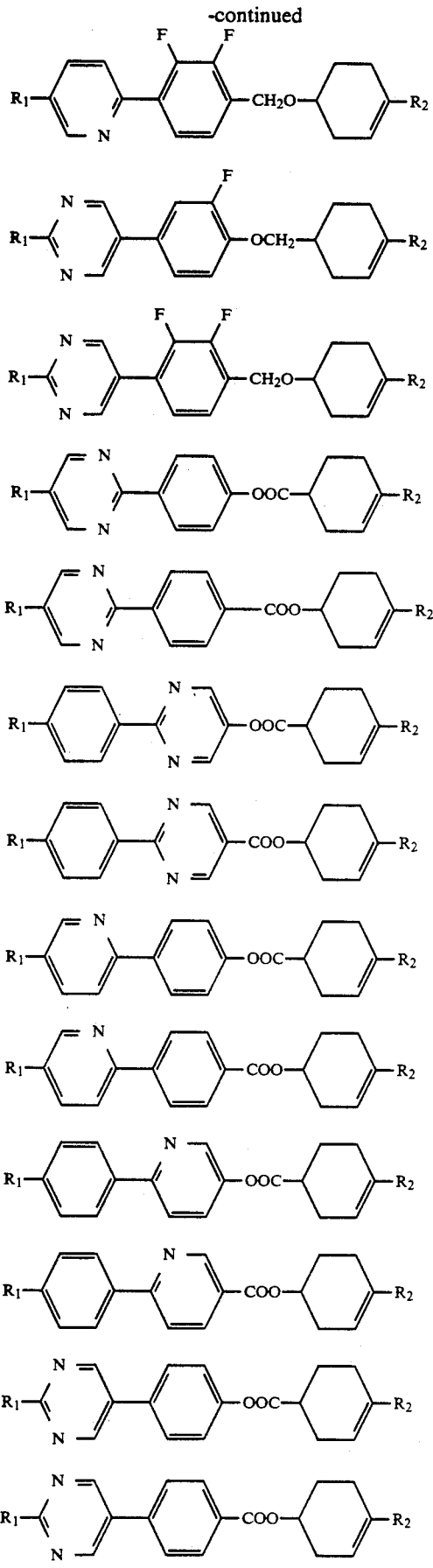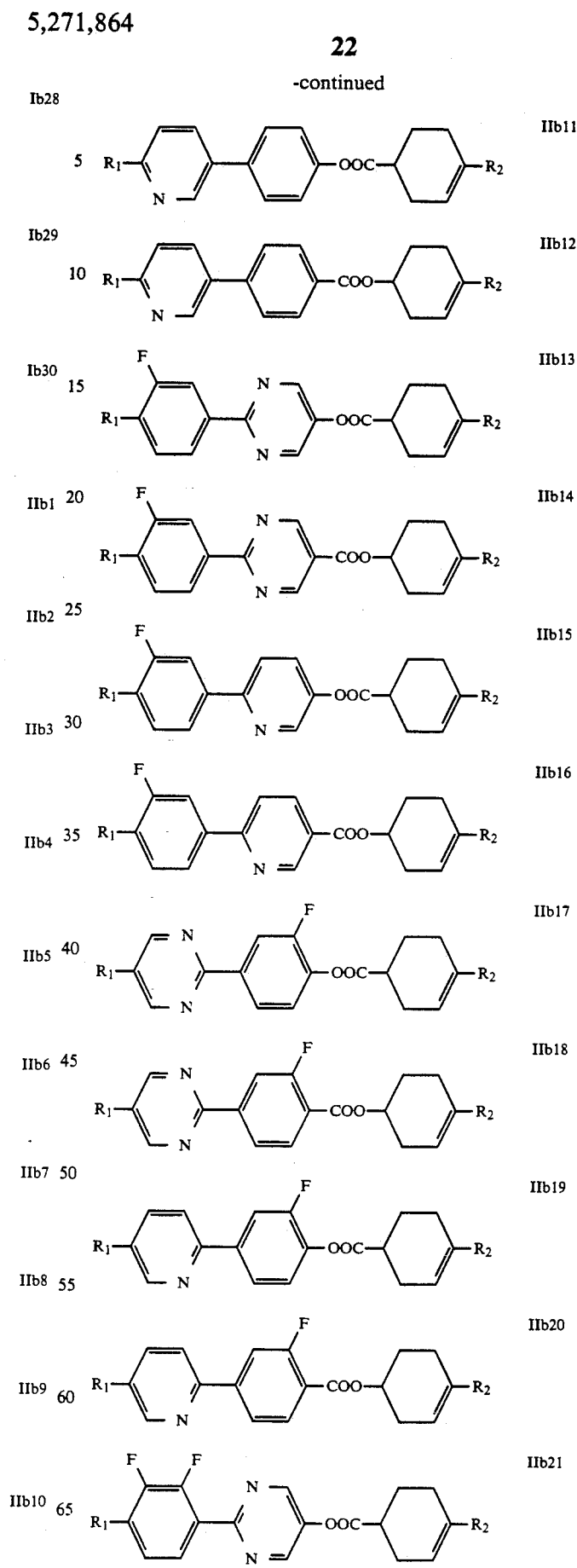

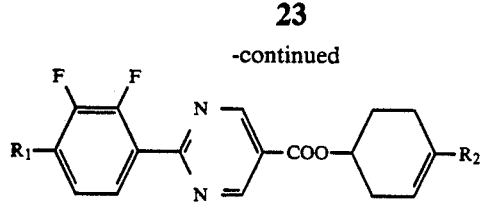 IIb22
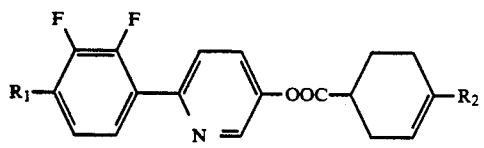 IIb23
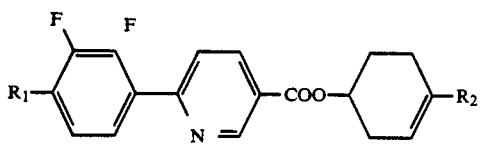 IIb24
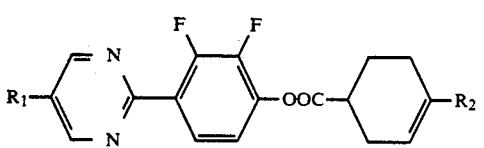 IIb25
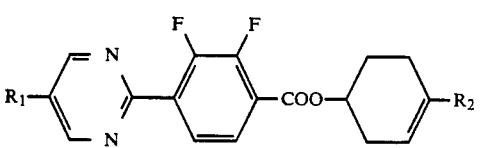 IIb26
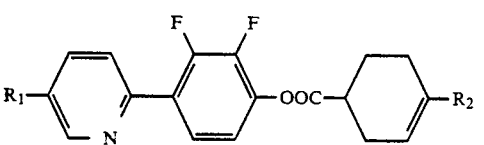 IIb27
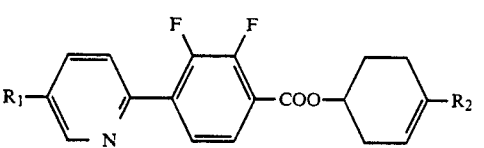 IIb28
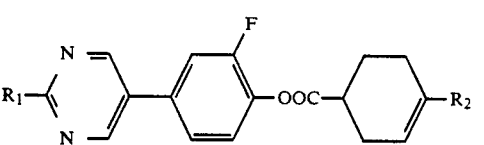 IIb29
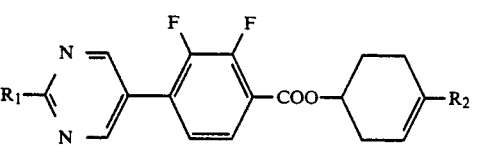 IIb30
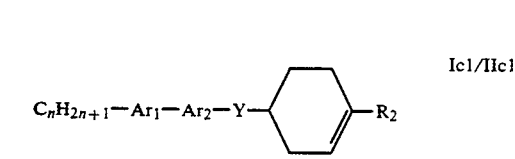 Ic1/IIc1
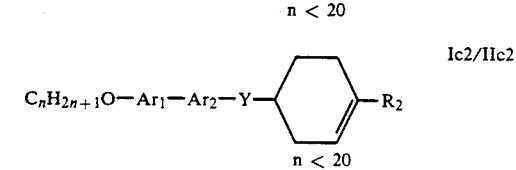 Ic2/IIc2
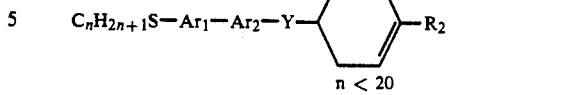 Ic3/IIc3
$C_nH_{2n+1}S-Ar_1-Ar_2-Y$ 
n < 20
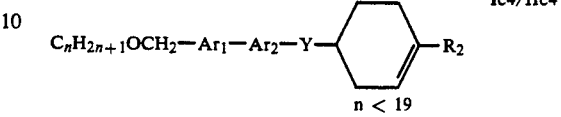 Ic4/IIc4
$C_nH_{2n+1}OCH_2-Ar_1-Ar_2-Y$
n < 19
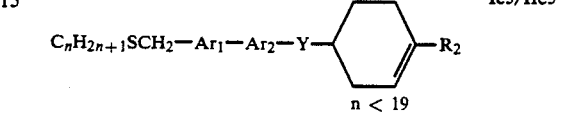 Ic5/IIc5
$C_nH_{2n+1}SCH_2-Ar_1-Ar_2-Y$
n < 19
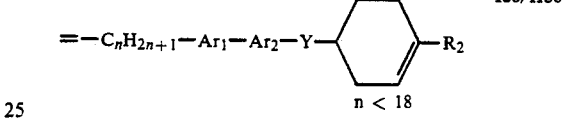 Ic6/IIc6
$=C_nH_{2n+1}-Ar_1-Ar_2-Y$
n < 18
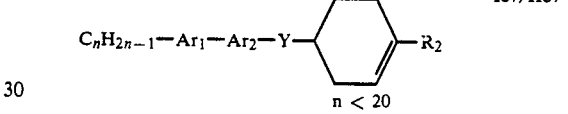 Ic7/IIc7
$C_nH_{2n-1}-Ar_1-Ar_2-Y$
n < 20
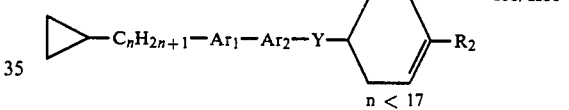 Ic8/IIc8
n < 17
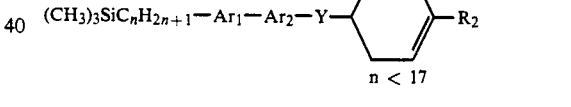 Ic9/IIc9
$(CH_3)_3SiC_nH_{2n+1}-Ar_1-Ar_2-Y$
n < 17
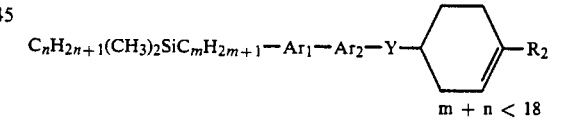 Ic10/IIc10
$C_nH_{2n+1}(CH_3)_2SiC_mH_{2m+1}-Ar_1-Ar_2-Y$
m + n < 18
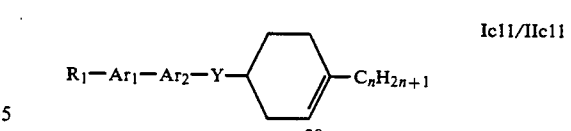 Ic11/IIc11
n < 20
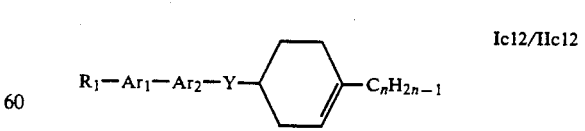 Ic12/IIc12
n < 20
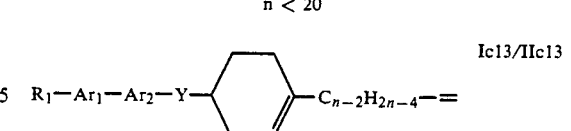 Ic13/IIc13
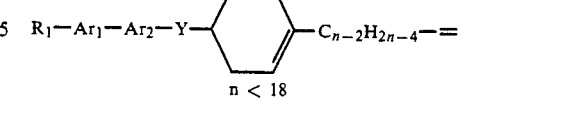
n < 18

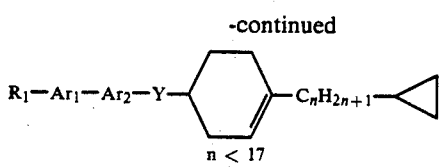 Ic14/IIc14
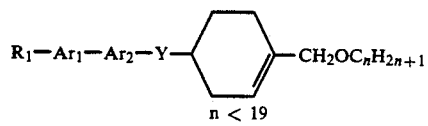 Ic15/IIc15
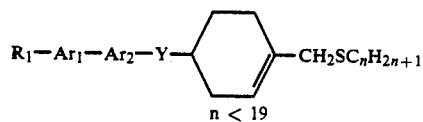 Ic16/IIc16
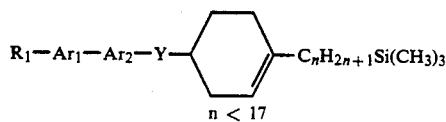 Ic17/IIc17
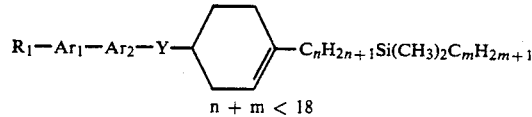 Ic18/IIc18
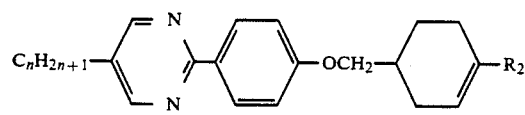 Id1
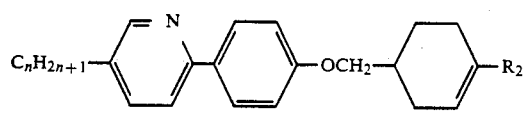 Id2
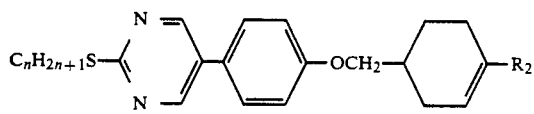 Id3
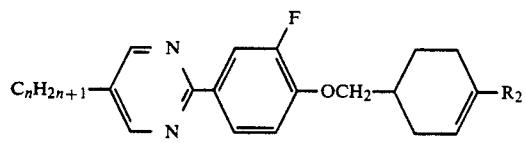 Id4
 Id5
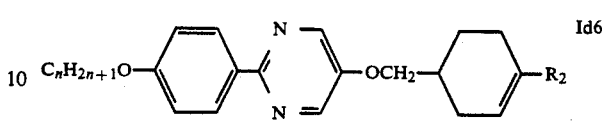 Id6
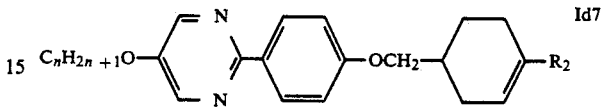 Id7
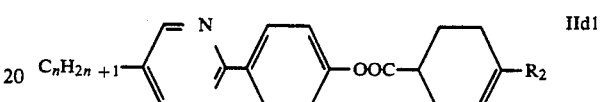 IId1
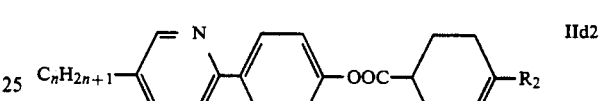 IId2
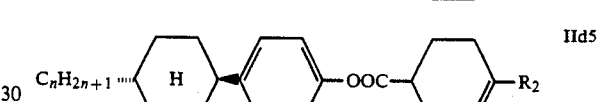 IId5
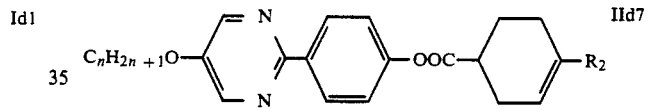 IId7
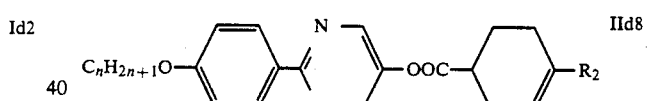 IId8
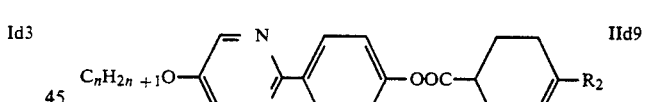 IId9
The following compounds have been synthesized:
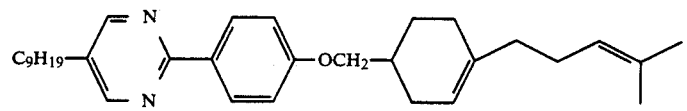 MDW343
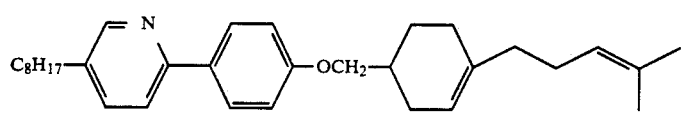 MDW555
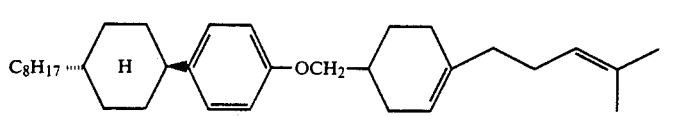 MDW569

-continued

| Structure | Label |
|---|---|
| C₁₀H₂₁O-pyrimidine-C₆H₄-OCH₂-cyclohexene-CH₂CH₂CH=C(CH₃)₂ | MDW580 |
| C₁₀H₂₁O-pyrimidine-C₆H₄-OCH₂-cyclohexene-CH₃ | MDW590 |
| C₁₀H₂₁-pyrimidine-C₆H₄-OCH₂-cyclohexene-CH₂CH₂CH=C(CH₃)₂ | MDW523 |
| C₁₀H₂₁O-pyrimidine-C₆H₄-OCH₂-cyclohexene-CH₃ | MDW589 |
| C₁₀H₂₁O-C₆H₄-pyrimidine-OCH₂-cyclohexene-CH₂CH₂CH=C(CH₃)₂ | MDW579 |
| C₁₀H₂₁S-pyrimidine-C₆H₄-OCH₂-cyclohexene-CH₂CH₂CH=C(CH₃)₂ | MDW556 |
| C₈H₁₇-pyrimidine-C₆H₃(F)-OCH₂-cyclohexene-CH₂CH₂CH=C(CH₃)₂ | MDW565 |
| C₁₀H₂₁-pyrimidine-C₆H₄-OOC-cyclohexene-CH₂CH₂CH=C(CH₃)₂ | MDW336 |
| C₈H₁₇-pyridine-C₆H₄-OOC-naphthalene-OOC-cyclohexene-CH₂CH₂CH=C(CH₃)₂ | MDW588 |
| C₈H₁₇-cyclohexyl(H)-C₆H₄-OOC-cyclohexene-CH₂CH₂CH=C(CH₃)₂ | MDW571 |
| C₁₀H₂₁O-pyrimidine-C₆H₄-OOC-cyclohexene-CH₂CH₂CH=C(CH₃)₂ | MDW578 |
| C₁₀H₂₁O-C₆H₄-pyrimidine-OOC-cyclohexene-CH₃ | MDW583 |

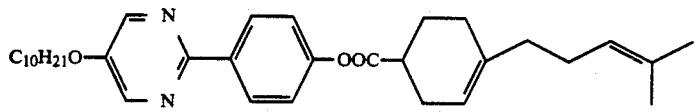

MDW577

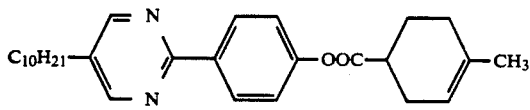

MDW576

When used in the above formulas, $R_1$, $R_2$, $Ar_1$, $Ar_2$, Y, $Y_1$ and $Y_2$ are the same as defined in the general formulas I and II, above.

Many of the compounds of the subject invention, specifically cyclohexenyl compounds wherein $R_1$ and $R_2$ are achiral groups, do not possess an enantiotropic or monotropic ferroelectric (smectic C*) liquid crystal phase. However, when these compounds are mixed with a chiral, nonracemic FLC dopant, such as MDW232 (below), and a known FLC host material, such as the phenylpyrimidine host material MX5343 (see Table 4), mixtures are produced which possess ferroelectric smectic C* phases. These mixtures exhibit improved tilt angle, C* pitch, switching speed and mixing properties relative to FLC mixtures comprising analogous cyclohexyl compounds.

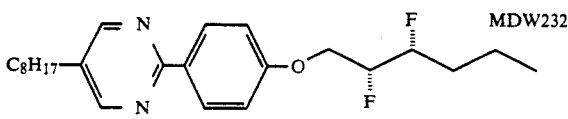

MDW232

Table 2 summarizes the tilt angle, C* pitch, rise time, melting point and supercooling point of mixtures comprising 20% (w/w) of the subject cyclohexenyl compounds or, alternatively, 20% (w/w) of cyclohexyl compounds, 10% (w/w) of the chiral dopant MDW232, and 70% (w/w) of the phenylpyrimidine host MX5343. In Table 2, the melting and supercooling points are given in °C., C* pitch is given in µm, tilt angles are given in degrees, and rise times were measured under an applied electric field strength of ±5 volts and given in µsec/µm.

As shown in Table 2, mixtures containing the cyclohexenyl compounds of the present invention possess a longer helix pitch in the smectic C* phase relative to mixtures containing analogous cyclohexyl compounds. In addition, the subject cyclohexenyl compounds impart improved mixing properties to FLC mixtures as compared to their cyclohexyl counterparts. Specifically, mixtures comprising the cyclohexenyl compounds have lower melting and supercooling points and, therefore, lower temperatures of crystallization. Moreover, mixtures containing the subject cyclohexenyl compounds exhibit a lower tilt angle than mixtures containing analogous cyclohexyl compounds. The tilt angle of mixtures comprising cyclohexenyl compounds approach 22.5°, the optimal tilt angle for FLC materials used in direct drive, flat panel display applications. Finally, as can be seen from Table 3, FLC mixtures containing the subject cyclohexenyl compounds exhibit smectic C* phases over a broader temperature range than FLC mixtures containing analogous cyclohexyl compounds.

EXAMPLES

EXAMPLE 1

Synthesis of Cyclohexenylmethyl Ethers

This example illustrates the procedures for synthesis of cyclohexenyl ethers (Scheme I, path A) by detailing the synthesis of the cyclohexenyl ether, 2-(4,-[(4-(4-methyl-3-pentenyl)-3-cyclohexenyl)-methylenoxy]-phenyl}-5-nonylpyrimidine MDW343 (I, where $Y_1$-=—O—$CH_2$—, $R_1$=$C_9H_{19}$ and $R_2$=4-methyl-3-pentene).

Ethyl acrylate (25.5 ml, 0.235 mol) was introduced into a 500 ml oven-dried round bottom flask containing a magnetic stir bar, along with anhydrous toluene (235 ml) and aluminum chloride (3.14 g, 23.5 mmol). The resulting solution was cooled to 0° C., after which freshly distilled mycrene (40 ml, 0.235 mmol) was added dropwise over a period of 30 minutes. The reaction mixture was then stirred for 5 hr at 0° C., and allowed to sit in a 4° C. refrigerator overnight. The resulting yellow mixture was placed in an extraction funnel, and washed with two 200 ml aliquots of 1% HCl. The first acid wash was cloudy, the second was clear. The reaction mixture was further washed with 100 ml water, then with 100 ml saturated sodium chloride, and dried over a combination of sodium sulfate and potassium carbonate. The mixture was filtered through celite, and the solvent removed in vacuo. The resulting liquid was distilled at 107°-109° C. at 1 mm Hg to afford 37.2 g (67% yield) of the product, ethyl 4-(4- methyl-3-pentenyl)-3-cyclohexen-1-carboxylate, as a colorless liquid.

Ethyl 4-(4-methyl-3-pentenyl)-3-cyclohexen-1-carboxylate (30g or 0.127 mol), water (127 ml), and potassium hydroxide (24.4 g or 0.444 mol) were added to a 250 ml round bottom flask equipped with a stir bar. A reflux condenser was attached to the flask, and the mixture was stirred under reflux for 16 hours. Concentrated HCl (40 ml), water (40 ml), and ice (ca. 40 g) were added to an extraction funnel. The reaction mixture was then added to the funnel, and the mixture extracted with dichloromethane (100 ml). After two further extractions with 50 ml aliquots of dichloromethane, the combined organic extracts were dried with sodium sulfate. The solvent was removed in vacuo, leaving a slightly yellow oil (26.3 g) which crystallized upon standing. The solid was recrystallized from a mixture of methanol (70 ml) and water (25 ml), giving fine white needles (15.3 g) with a melting point of 55.5°-57.5° C. The mother liquor was concentrated in vacuo and recrystallized again (87 ml methanol, 35 ml water), affording an additional 6.0 g of needles having a melting point of 53°-54° C. The total yield of the product, 4-(4-methyl-3-pentenyl)-3-cyclohexen-1-carboxylic acid, was 21.3 g (81%).

4-(4-methyl-3-pentenyl)-3-cyclohexen-1-methanol was synthesized as follows. An oven-dried refluxing condenser and an oven-dried 125 ml pressure-equalized addition funnel was attached to an oven-dried 500 ml 3-neck round-bottom flask. A magnetic stir bar was added, along with lithium aluminum hydride (LAH; 3.64 g or 96 mmol). Tetrahydrofuran (100 ml) was then added, and the suspension was cooled to 0° C. in an ice bath. A solution of 4-(4-methyl-3-pentenyl)-3-cyclohexen-1-carboxylic acid (10 g or 48 mmol) and THF (30 ml) was placed in the addition funnel, and the acid solution was added dropwise to the LAH suspension over a period of about 10 minutes. The residual acid in the addition funnel was washed into the LAH suspension with two further 10 ml aliquots of THF, the ice bath was removed, and the reaction was allowed to stir for at least 3 hours. After stirring, the reaction was again cooled to 0° C. and 18 ml water (5 ml water for each g LAH) was placed in the addition funnel. A further 50 ml THF was added to the reaction mixture to make the LAH suspension less viscous, and the evolved hydrogen gas was allowed to escape. The water was added dropwise to the LAH suspension over a period of about 30 minutes. The ice bath was then removed and the gray suspension was allowed to stir (approximately 3 hours) until the reaction turned white with no residual gray color. The reaction mixture was then acidified with 2M HCl (150 ml), extracted with a 1:1 (v/v) ethyl acetate:hexane mixture (shaken with saturated NaCl), dried over a mixture of anhydrous $Na_2SO_4$ and $K_2CO_3$, filtered, and rotary evaporated. Thin layer chromatography using 1:4 (v/v) ethyl acetate:hexane showed the product at Rf 0.17, with small impurity at Rf 0.0 and Rf 0.26. Removal of solvent, at 92°-95° C., 1 torr, gave 8.89 g (95%) of 4-(4-methyl-3-pentenyl)-3-cyclohexen-1-methanol, as a slightly yellow oil.

To produce 4-(4-methyl-3-pentenyl)-3-cyclohexen-1-methanol toluenesulfonate, 4-(4-methyl-3-pentenyl)-3-cyclohexen-1-methanol (7.89 g, 40.6 mmol) and pyridine (8.2 ml, 101.6 mmol) were added to a 50 ml oven-dried round bottom flask. The mixture was stirred in an ice bath at 0° C. for 15 minutes. p-toluenesulfonyl chloride (TsCl; 8.13 g or 42.7 mmol) was then added, the reaction mixture stirred for a further 60 minutes at 0° C., and the mixture allowed to sit overnight in a −20° C. cooler. The reaction was found to be complete by TLC after 16 hours. The Rf of the product in 1:4 (v:v) ethyl acetate:hexane was 0.42. 10 ml each of THF and water were then added, the reaction mixture stirred at room temperature for 1 hour, and then extracted with 2 N HCl (74 ml) and ethyl acetate. The combined organic layers were washed with saturated NaCl, dried over sodium sulfate and potassium carbonate, and rotary evaporated to produce 14.1 g (99%) of 4-(4-methyl-3-pentenyl)-3-cyclohexen-1-methanol toluenesulfonate, as a light yellow, non-viscous oil.

2-{4'-[(4-(4-methyl-3-pentenyl)-3-cyclohexenyl)-methylenoxy]-phenyl}-5-nonylpyrimidine was synthesized as follows. 2-[4'-phenol]-5-decylpyrimidine (3.0 g, 10.1 mmol), 4-(4-methyl-3-pentenyl)-3-cyclohexen-1-methanol toluenesulfonate (3.5 g, 10.1 mmol), powdered cesium carbonate (3.4 g, 10.6 mmol), and dimethylformamide (30 ml) were added to a 50 ml round-bottom flask containing a stir bar. The reaction mixture was stirred under inert atmosphere at 75° C. for 4.5 hours. The reaction mixture was then poured into a separatory funnel containing 2 N HCl (60 ml), and extracted with a 1:1 (v/v) ethyl acetate:hexane solvent mixture. The combined organic layers were then washed with saturated NaCl, and dried over a mixture of anhydrous sodium sulfate and potassium carbonate. The product was purified by recrystallization from 5:1 (v/v) acetonitrile:ethyl acetate (ca. 200 ml), giving a light yellow solid (4.3 g). The solid was next purified by flash chromatography on a silica column using 4:1 (v/v) hexane:ethyl acetate as the eluent, and rotary evaporated. The solid was further purified by filtration (0.5 μm filter) using dichloromethane as the solvent, and rotary evaporated. Finally, the product was recrystallized from hexane (30 ml) to afford 3.5 g (74% yield) of 2-{4'-[(4-(4-methyl-3-pentenyl)-3-cyclohexenyl)-methylenoxy]-phenyl}-5-nonylpyrimidine, as a white solid.

Example 1a

Synthesis of
2-(4'-[(4-(4-methyl-3-pentenyl)-3-cyclohexenyl)-methylenoxy]-phenyl}-5-decylpyrimidine (MDW523)

To make 3-(4'-[(4-(4-methyl-3-pentenyl)-3-cyclohexenyl)-methylenoxy]-phenyl}-6-decylpyrimidine, the same procedure for making 2-{4,-[(4-(4-methyl-3-pentenyl)-3-cyclohexenyl)-methylenoxy]-phenyl)-5-nonylpyrimidine was followed with the exception that 3-[4'-phenol]-6-decylpyrimidine was used in place of 2-[4,-phenol]-5-nonylpyrimidine.

Example 1b

Synthesis of
2-(4'-[(4-(4-methyl-3-pentenyl)-3-cyclohexenyl)-methylenoxy]-phenyl}-5-octylpyridine (MDW555)

To make 2-{4'-[(4-(4-methyl-3-pentenyl)-3-cyclohexenyl)-methylenoxy]-phenyl}-5-octylpyridine, the same procedure for making 2-(4,-[(4-(4-methyl-3-pentenyl)-3-cyclohexenyl)-methylenoxy]-phenyl}-5-nonylpyrimidine was followed with the exception that 2-[4'-phenol]-5-octylpyridine was used in place of 2-[4'-phenol]-5-nonylpyrimidine.

Example 1c

Synthesis of
5-(4'-[(4-(4-methyl-3-pentenyl)-3-cyclohexenyl)-methylenoxy]phenyl}-2-decylthiopyrimidine (MDW556)

To make 5-{4'-[(4-(4-methyl-3-pentenyl)-3-cyclohexenyl)-methylenoxy]-phenyl}-2-decylthiopyrimidine, the same procedure for making 2-{4'-[(4-(4-methyl-3-pentenyl)-3-cyclohexenyl)-methylenoxy]-phenyl}-5-nonylpyrimidine was followed with the exception that 5-[4'-phenol]-2-decylthiopyrimidine was used in place of 2-[4'-phenol]-5-nonylpyrimidine.

Example 1d

Synthesis of
2-{4'-[(4-(4-methyl-3-pentenyl)-3-cyclohexenyl)-methylenoxy]-3,-flourophenyl}-5-octylpyrimidine (MDW565)

To make 2-(4'-[(4-(4-methyl-3-pentenyl)-3-cyclohexenyl)-methylenoxy]-3'-fluorophenyl-5-octylpyrimidine, the same procedure for making 2-{4'-[(4-(4-methyl-3-pentenyl)-3-cyclohexenyl)-methylenoxy]-phenyl}-5-nonylpyrimidine was followed with the exception that 2-[3'-fluoro-4'-phenol]-5-octylpyrimidine was used in place of 2-[4'-phenol]-5-nonylpyrimidine.

Example 1e

Synthesis of 1-{4'-[(4-(4-methyl-3-pentenyl)-3-cyclohenenyl)-methylenoxy]-phenyl}-4-octylcyclohexane (MDW569)

To make 1-{4,-[(4-(4-methyl-3-pentenyl)-3-cyclohexenyl)-methylenoxy]-phenyl)-4-octylcyclohexane, the same procedure for making 2-{4'-[(4-(4-methyl-3-pentenyl)-3-cyclohexenyl)-methylenoxy]-phenyl}-5-nonylpyrimidine was followed with the exception that 1-[4'-phenol]-4-octylcyclohexane was used in place of 2-[4'-phenol]-5-nonylpyrimidine.

Example 1f

Synthesis of 2-(4,-decyloxyphenyl)-5-[4-(4-methyl-3-pentenyl)-3-cyclohexenyl)-methylenoxy]-primidine (MDW579)

To make2-(4'-decyloxyphenyl)-5-[4-(4-methyl-3-pentenyl)-3-cyclohexenyl)-methylenoxy]-pyrimidine, the same procedure for making 2-(4'-[(4-(4-methyl-3-pentenyl)-3-cyclohexenyl)-methylenoxy]-phenyl}-5-nonylpyrimidine was followed with the exception that 2-(4'-decyloxyphenyl)-5-ol-pyrimidine was used in place of 2-[4'-phenol]-5-nonylpyrimidine.

Example 1g

Synthesis of 2-(4'-[(4-(4-methyl-3-pentenyl)-3-cyclohexenyl) methylenoxy] phenyl}- 5-decyloxypyrimidine (MDW580)

To make 2-{4'-[(4-(4-methyl-3-pentenyl)-3-cyclohexenyl)methylenoxy]phenyl}-5-decyloxypyrimidine, the same procedure for making 2-(4'-[(4-(4-methyl-3-pentenyl)-3-cyclohexenyl)-methylenoxy]-phenyl}-5-nonylpyrimidine was followed with the exception that 2-[4'-phenol]-5-decyloxypyrimidine was used in place of 2-[4'-phenol]-5-nonylpyrimidine.

Example 1h

Synthesis of 2-{4'-[(4-(4-methyl-3-pentenyl)-3-cyclohexenyl)-methylenoxy]-phenyl) -5-decylpyrazine To make 2-{4'-[(4-(4-methyl-3-pentenyl)-3-cyclohexenyl)-methylenoxy]-phenyl}-5-decylpyrazine, the same procedure for making 2-(4'-[(4-(4-methyl-3-pentenyl)-3-cyclohexenyl)-methylenoxy]-phenyl}-5-nonylpyrimidine is followed with the exception that 2-[4'-phenol]-5-decylpyrazine is used in place of 2-[4'-phenol]-5-nonylpyrimidine.

Example 1j

Synthesis of 2-{4'-[(4-(4-methyl-3-pentenyl)-3-cyclohexenyl)-methylenoxy]-phenyl}-5-decylpyridazine To make 2-{4'-[(4-(4-methyl-3-pentenyl)-3-cyclohexenyl)-methylenoxy]-phenyl}-5-decylpyridazine, the same procedure for making 2-(4'-[(4-(4-methyl-3-pentenyl)-3-cyclohexenyl)-methylenoxy]-phenyl}-5-nonylpyrimidine is followed with the exception that 2-[4'-phenol]-5-decylpyridazine is used in place of 2-[4'-phenol]-5-nonylpyrimidine.

Example 2

Synthesis of Cyclohexene Carboxylic Acid Esters

This example illustrates the procedures (Scheme I, path B) for synthesis of cyclohexenyl esters by detailing the synthesis of the trans cyclohexenyl ester, 2-(4'-[(4-(4-methyl-3-pentenyl)-3-carbonyloxy]-phenyl}-5-decylpyrimidine MDW336 (I, where $Y_2$=—OOC—, $R_1$=$C_{10}H_{21}$ and $R_2$=4-methyl-3-pentene).

Ethyl acrylate (25.5 ml, 0.235 mol) was introduced into a 500 ml oven-dried round bottom flask containing a magnetic stir bar, along with anhydrous toluene (235 ml) and aluminum chloride (3.14 g, 23.5 mmol). The resulting solution was cooled to 0° C., after which freshly distilled mycrene (40 ml, 0.235 mmol) was added dropwise over a period of 30 minutes. The reaction mixture was then stirred for 5 hr at 0° C., and allowed to sit in a 4° C. refrigerator overnight. The resulting yellow mixture was placed in an extraction funnel, and washed with two 200 ml aliquots of 1% HCl. The first acid wash was cloudy, the second was clear. The reaction mixture was further washed with 100 ml water, then with 100 ml saturated sodium chloride, and dried over a combination of sodium sulfate and potassium carbonate. The mixture was filtered through celite, and the solvent removed in vacuo. The resulting liquid was distilled at 107°–109° C. at 1 mm Hg to afford 37.2 g (67% yield) of the product, ethyl 4-(4-methyl-3-pentenyl)-3-cyclohexen-1-carboxylate, as a colorless liquid.

Ethyl 4-(4-methyl-3-pentenyl)-3-cyclohexen-I-carboxylate (30 g or 0.127 mol), water (127 ml), and potassium hydroxide (24.4 g or 0.444 mol) were added to a 250 ml round bottom flask equipped with a stir bar. A reflux condenser was attached to the flask, and the mixture was stirred under reflux for 16 hours. Concentrated HCl (40 ml), water (40 ml), and ice (ca. 40 g) were added to an extraction funnel. The reaction mixture was then added to the funnel, and the mixture extracted with dichloromethane (100 ml). After two further extractions with 50 ml aliquots of dichloromethane, the combined organic extracts were dried with sodium sulfate. The solvent was removed in vacuo, leaving a slightly yellow oil (26.3 g) which crystallized upon standing. The solid was recrystallized from a mixture of methanol (70 ml) and water (25 ml), giving fine white needles (15.3 g) with a melting point of 55.5°–57.5° C. The mother liquor was concentrated in vacuo and recrystallized again (87 ml methanol, 35 ml water), affording an additional 6.0 g of needles having a melting point of 53°–54° C. The total yield of the product,4-(4-methyl-3-pentenyl)-3-cyclohexen-1-carboxylicacid, was 21.3 g (81%).

2-{4'-[(4-(4-methyl-3-pentenyl)-3-cyclohexenyl)-carbonyloxy]-phenyl}-5-decylpyrimidine was synthesrzec as follows. 4-(4-methyl-3-pentenyl)-3-cyclohexen-1-carboxylic acid (400 mg, 1.9 mmol) and oxalyl chloride (1 ml, 3.8 mmol) were added to a 10 ml round bottom flask containing a stir bar. The reaction mixture was stirred for approximately 45 minutes, rotary evaporated, and then placed under high vacuum (1 torr) for 1 hour. 5-decyl-2-(4'-hydroxyphenyl)-pyrimidine (630 mg, 1.92 mmol), anhydrous tetrahydrofuran (3 ml), dimethylaminopyridine (DMAP; 3 mg), and triethylamine (3 ml) were then added. The reaction mixture was then stirred for 14 hours, poured into a dilute HCl solution, and extracted with ethyl acetate. The combined organic layers were washed with saturated NaCl, dried over a mixture of $Na_2SO_4$ and $K_2CO_3$, and rotary evaporated. The product was purified by chromatography using a 9:1 (v/v) hexane:ethyl acetate mixture, affording 824 mg (85% yield) of a white solid. The product, 2-(4'-[(4-(4-methyl-3-pentenyl)-3-cyclohexenyl)-carbonyloxy]- phenyl}-5-decylpyrimidine, was further purified by sequential recrystallization from ethanol then from a 9:1 (v:v) acetonitrile:ethyl acetate mixture to afford 601 mg (62% yield) of a fine white crystal material.

Example 2a

Synthesis of 1-{4'-[(4-(4-methyl-3-pentenyl)-3-cyclohexenyl)-carbonyloxy]-phenyl}-4-octylcyclohexane (MDW571)

To make 1-{4'-[(4-(4-methyl-3-pentenyl)-3-cyclohexenyl)-carbonyloxy]-phenyl}-4-octylcyclohexane, the same procedure for making 2-{4'-[(4-(4-methyl-3-pentenyl)-3-cyclohexenyl)-carbonyloxy]-phenyl}-5-decylpyrimidine was followed with the exception that I-[4'-phenol]-4-octylcyclohexane was used in place of 2-[4'-phenol]-5-decylpyrimidine.

Example 2b

Synthesis of 2-(4'-[(4-methyl-3-cyclohexenyl)-carbonyloxy]-phenyl}-5-decylpyrimidine (MDW576)

To make 2-{4'-[(4-methyl-3-cyclohexenyl)-carbonyloxy]-phenyl}-5-decylpyrimidine, the same procedure for making 2-(4'-[(4-(4-methyl-3-pentenyl)-3-cyclohexenyl)-carbonyloxy]-phenyl}-5-decylpyrimidine was followed with the exception that distilled isoprene was used in place of mycrene.

Example 2c

Synthesis of 2-(4'-decyloxyphenyl)-5-[(4-methyl-3-pentenyl)-3-cyclohexenyl)-carbonyloxy]-pyrimidine (MDW577)

To make 2-(4'-decyloxyphenyl)-5-[(4-methyl-3-pentenyl)-3-cyclohexenyl)-carbonyloxy]-primidine, the same procedure for making 2-{4'-[(4-(4-methyl-3-pentenyl)-3-cyclohexenyl)-carbonyloxy]-phenyl}-5-decylpyrimidine was followed with the exception that 2-(4'-decyloxyphenyl)-5-ol-pyrimidine was used in place of 2-[4'-phenol]-5-decylpyrimidine.

Example 2d

Synthesis of 2-{4'-[(4-methyl-3-cyclohexenyl)-carbonyloxy]-phenyl}-5-decyloxypyrimidine (MDW578)

To make 2-(4'-[(4-methyl-3-cyclohexenyl)-carbonyloxy]-phenyl}-5-decyloxypyrimidine, the same procedure for making 2-{ 4'-[(4-(4-methyl-3-pentenyl)-3-cyclohexenyl)-carbonyloxy]-phenyl}-5-decylpyrimidine was followed with the exception that 2-[4'-phenol]-5-decyloxypyrimidine was used in place of 2-[4'-phenol]-5-decylpyrimidine.

Example 3

Synthesis of Straight-chain Alkylcyclohexene Carboxylic Acid Esters

This example illustrates the procedures for synthesis of straight-chain alkylcyclohexenyl esters by detailing the synthesis of the alkylcyclohexenyl ester, 2-[4'-(4-pentyl-3-cyclohexencarbonyloxy)-phenyl]-5-decylpyrimidine (I, where $Y_2$=—OOC—, $R_1$=$C_{10}H_{21}$ and $R_2$ =pentyl).

n-bromosuccinimide (5.34 g) is added to a solution of isoprene (2.45 g) in carbon tetrachloride (100 ml), and the solution is stirred for 24 hours. The product and solvent are then fractionally distilled away from the succinimide, resulting in a partially concentrated solution of c-bromomethylbutadiene. The bromomethylbutadiene solution is chilled (−20° C.), and a 2N tetrahydrofuran solution of butylmagnesium bromide (15 ml) is then added. After stirring for 4 hours, the solution is treated with a 1 M phosphate buffer solution (pH 7). The organic layer is dried over sodium sulfate, and the reaction mixture is fractionally distilled to produce the product, 2-pentyl-1,3-butadiene, as a non-viscous liquid.

Ethyl acrylate (1.92 ml) is added to toluene (15 ml) and aluminum chloride (215 mg). The resulting solution is cooled to 0° C., after which 2-pentyl-1,3-butadiene (2.0 g) is added dropwise over a period of 30 minutes. The reaction mixture is then stirred for 5 hr at 0° C., and stored in a 4° C. refrigerator overnight. The resulting mixture is placed in an extraction funnel, and washed with two 200 ml aliquots of 1% HCl. The reaction mixture is further washed with 100 ml water, then with 100 ml saturated sodium chloride, and dried over a combination of sodium sulfate and potassium carbonate. The mixture is filtered through celite, and the solvent removed in vacuo. The resulting liquid is distilled at 107°–109° C. at 1 mm Hg to produce ethyl 4-pentyl-3-cyclohexen-1-carboxylate.

Ethyl 4-pentyl-3-cyclohexen-l-carboxylate (3.0 g) is added to a solution of water (27 ml) and potassium hydroxide (2.6 g). The mixture is stirred under reflux for 16 hours. The reaction mixture is then neutralized with a mixture of concentrated HCl (40 ml), water (40 ml), and ice (ca. 40 g), and the mixture extracted with dichloromethane (100 ml). The combined organic extracts are dried with sodium sulfate, and the solution concentrated in vacuo. The solid is recrystallized from a mixture of methanol (70 ml) and water (25 ml), resulting in the product, 4-pentyl-3-cyclohexen-1-carboxylic acid.

4-pentyl-3-cyclohexen-1-carboxyl chloride is synthesized as follows. To a flask containing 4-pentyl-3-cyclohexen-1-carboxylic acid (2.3 g) in toluene (12 ml) is added oxalyl chloride (3.08 ml). The reaction mixture is stirred at room temperature for three hours, after which the solvent and excess oxalyl chloride are removed in vacuo to produce the product, 4-pentyl-3-cyclohexen-1-carboxyl chloride.

2-{4'-[(4-pentyl-3-cyclohexenyl)-carbonyloxy]-phenyl}-5-decylpyrimidine is synthesized as follows. Tetrahydrofuran (35 carboxyl chloride (2.3 g) and 5-decyl-2-(4'-hydroxyphenyl)-pyrimidine (3.66 g). The reaction mixture is stirred until homogenous, then triethylamine (2.5 ml) is added. The reaction mixture immediately turns turbid. The turbid solution is stirred 1 hour, poured into a dilute (5%) hydrochloric acid solution, and extracted with ethyl acetate. The combined organic layers are then extracted with saturated sodium chloride, dried over sodium sulfate, and the solvent removed in vacuo. The product is purified by flash chromatography using 10% ethyl acetate in hexane as the eluent, and recrystallized from acetonitrile to produce the product, 2-{4'-[(4-pentyl-3-cyclohexenyl)-carbonyloxy]-phenyl)-5-decylpyrimidine.

Example 3a

Synthesis of 2-{4'-[(4-pentyl-3-cyclohexenyl)-methylenoxy]-phenyl}-5-nonylpyrimidine To make 2-(4'-[(4-pentyl-3-cyclohexenyl)-methylenoxy]-phenyl}-5-nonylpyrimidine, the same procedure for making 2-{4'-[(4-pentyl-3-cyclohexenyl)- carbonyloxy]-phenyl}-5-decylpyrimidine was followed through the preparation of 4-pentyl-3-cyclohexen-1-carboxylic acid. The straight-chain alkylcyclohexenyl ether, 2-{4'-[(4-pentyl-3-cyclohexenyl)-methylenoxy]-phenyl}-5-nonylpyrimidine, was then prepared as follows.

A solution of 4-pentyl-3-cyclohexen-l-carboxylic acid (3.4 g) in tetrahydrofurn (THF; 55 ml) was added dropwise to a cold (0° C.) solution of lithium aluminim hydride (1.37 g) in tetrahydrofuran (THF, 55 ml), in a flask equipped with a condenser. The reaction mixture was stirred at room temperature for at least three hours, re-cooled to 0° C., and water (8 ml) was then added dropwise. An additional 55 ml of THF was added, and the reaction mixture stirred for three hours. The reaction mixture was then acidified with 2 M HCl (150 ml), and extracted with a 1:1 (v:v) ethyl acetate:hexane mixture. The combined organic layers were extracted with saturated sodium chloride and dried over sodium sulfate. The solvent was removed in vacuo, and the resultant oil was distilled (92°–95° C. at c.a. 1 mm Hg) to produce 4-pentyl-3-cyclohexen-1-methanol.

To a solution of 4-pentyl-3-cyclohexen-1-methanol (3.0 g) in pyridine (3.3 ml) at 0° C. was added p-toluenesulfonyl chloride (3.3 g). The reaction was stirred in an ice bath for 2 hours, and then stored at −20° C. for a further 16 hours. The reaction mixture was then poured into 2 M HCl (75 ml) and extracted with ethyl acetate. The combined organic layers were extracted with saturated sodium chloride and dried over sodium sulfate. The solvent was removed in vacuo to produce 4-pentyl-3-cyclohexen-1-methanol toluenesulfonate.

To a solution of 4-pentyl-3-cyclohexen-1-methanol toluenesulfonate (5.5 g) and 5-nonyl-2-(4'-hydyroxy-phenyl)-pyrimidine (4.85 g) in dimethylformamide (50 ml) was added powdered cesium carbonate (5.33 g). The reaction mixture was stirred 16 hours at room temperature, then poured into 2 M HCl (60 ml), and extracted with a 1:1 (v:v) mixture of ethyl acetate:hexane. The combined organic layers were washed with saturated sodium chloride, dried over sodium sulfate, and the solvent was removed in vacuo. The solid compound was then filtered through silica gel using 4:1 (v:v) hexane:ethyl acetate, and the solvent was again removed in vacuo. The product, 2-(4'-[(4-pentyl-3-cyclohexenyl)-methylenoxy]-phenyl}-5-nonylpyrimidine, was again purified by sequential recrystallizations from acetonitrile and hexane.

Example 4

Synthesis of Cyclohexenyl Esters

This example illustrates the procedures (Scheme II, path B) for synthesis of cyclohexene esters (II, where $Y_2$=—COO—) by detailing the synthesis of the cyclohexenyl ester, 2-{4'-[(4-(4-methyl-3-pentenyl)-3-cyclohexenyl)-oxycarbonyl]-phenyl}-5-octylpyrimidine (II, where $R_1$=$C_8H_{17}$; $R_2$=4-methyl-3-pentyl; and $Y_2$=COO).

To prepare 4-(4-methyl-3-pentenyl)-3-cyclohexen-1-ol acetate, freshly distilled myrcene (30 ml), vinyl acetate (32 ml), and a teflon-coated magnetic stir bar are sealed together in a bomb tube. The tube is heated in an oil bath at 200° C., stirred for eight hours, then cooled to 0° C., at which temperature the tube is opened. The reaction mixture is fractionally distilled to give the Diels-Alder adduct as a clear liquid.

To prepare 4-(4-methyl-3-pentenyl)-3-cyclohexen-1-ol, potassium hydroxide (8.5 g) is added to a solution of 4-(4-methyl-3-pentenyl)-3-cyclohexen-1-ol acetate (17.0 g) in ethanol (150 ml), and the reaction mixture is stirred at room temperature for four hours. The mixture is then poured into a 1 M HCl solution (170 ml) and extracted with ethyl acetate. The combined organic layers are extracted with saturated sodium chloride, dried over sodium sulfate, and the solvent is then removed in vacuo.

2-{4'-[(4-(4-methyl-3-pentenyl))-3-cyclohexenyl)-oxycarbonyl]-phenyl)-5-octylpyrimidine is synthesized as follows. Tetrahydrofuran (33 ml) is added to a dry flask containing 4-(5'-octyl-2'-pyrimidyl)-benzoyl chloride (3.67 g) and 4-(4-methyl-3-pentenyl)-3-cyclohexen-1-ol (2.0 g). The reaction mixture is stirred until homogenous, then triethylamine (2.3 ml) is added. The reaction mixture immediately turns turbid. The turbid solution is stirred hour, poured into a dilute (5%) hydrochloric acid solution, and extracted with ethyl acetate. The combined organic layers are then extracted with saturated sodium chloride, dried over sodium sulfate, and the solvent removed in vacuo. The product is purified by flash chromatography using 10% ethyl acetate in hexane as the eluent, and recrystallized from acetonitrile to produce the product, 2-{4'-[(4-(4-methyl-3-pentenyl)-3-cyclohexenyl)-oxycarbonyl]-phenyl-}-5-octyl-pyrimidine.

Example 5

Synthesis of Cyclohexenyl Ethers

This example illustrates the procedures (Scheme II, path A) for synthesis of cyclohexenyl ethers (I, where $Y_1$=—$CH_2O$—) by detailing the synthesis of the cyclohexenyl ether, 2-(4'-[4-(4-methyl-3-pentenyl)-3-cyclohexenoxymethylene]-phenyl}-5-octylpyrimidine.

4-(4-methyl-3-pentenyl)-3-cyclohexen-l-ol was prepared as described in Example 4. To a flask containing 4-(4-methyl-3-pentenyl)-3-cyclohexen-1-ol (2.0 g) is added 4-(5,-octyl-2'-pyrimidyl)-benzyl toluenesulfonate (4.18 g) and dimethylformamide (33 ml). The reaction mixture is stirred until homogenous, then dry sodium hydride (0.3 g) is added. The mixture is stirred for an additional 36 hours, then poured into a 0.5 M HCl solution (30 ml) and extracted with a 1:1 (v:v) ethyl acetate:-hexane mixture. The combined organic layers are extracted with saturated sodium chloride and dried over sodium sulfate. The solvent is then removed in vacuo to produce the product, 2-{4'-[4-(4-methyl-3-pentenyl)-3-cyclohexenoxymethylene]-phenyl}-5-octylpyrimidine, as a white solid.

Example 6

Preparation of Cyclohexenyl Methyl Ether Phenylpyrimidine Host Material

This example illustrates the procedure for preparation of LC and FLC host material containing the cyclohexene containing compound of this invention by describing the preparation of the host MX6111 composition.

The host material MX6111 is mixed in the w/w proportions given in the following Table 4. Specifically, the host MX6111 composition is prepared by adding 20% (w/w) MDW343 to the phenylpyrimidine host material MX5343. MX5343 comprises the first eight components listed in Table 4, all of which are known in the art. The selected amounts of each compound are combined in a vial, heated until all materials have reached the isotropic phase, gently mixed until completely homogenous, then cooled. Certain properties of FLC mixtures containing cyclohexene compounds of this invention are listed in Tables 1 and 2.

Example 7

Comparison of Cyclohexane-based Smectic Mixtures with Cyclohexene-based Smectic Mixtures Two FLC mixtures were prepared:

Mixture A contained 20% (w/w) MDW342 (a methylcyclohexanyl ether) and 10% (w/w) MDW 206 (a chiral, nonracemic FLC dopant that is the $C_7$- homolog of MDW232) in the phenylpyrimidine host MX5343 (Table 3). Mixture B contained 20% (w/w) the cyclohexene MDW343 in place of the cyclohexane MDW342.

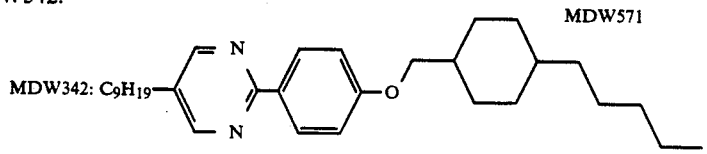

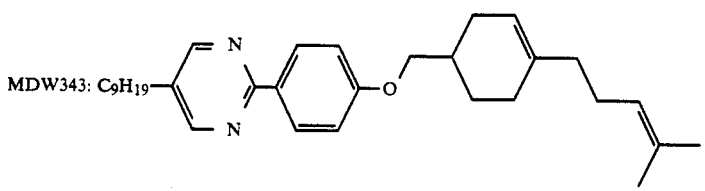

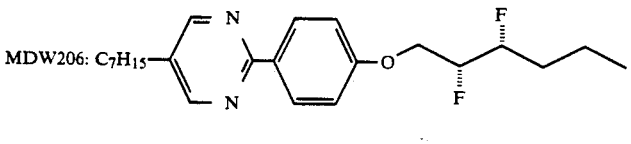

After 24 hours at 5° C., faint crystallization was observed under the microscope in Mixture A. In contrast, no crystals were observed in Mixture B under the same conditions after 72 hours at 5° C. Thus, Mixture B containing the cyclohexene component was found to be more stable to crystallization than Mixture A.

The invention has been described and illustrated by reference to several preferred embodiments, but it is not intended to limit the invention by doing so. For example, it is intended that the invention encompass not only the LC compounds described specifically herein, but also compositions or formulations in which these compounds are admixed with each other or with other compounds including other LC and FLC materials.

TABLE 1

Phase Properties of Representative Compounds of this Invention.

MDW336   I ⇌106 N ⇌83 C ⇌27/40 X

MDW343   I ⇌100 N ⇌89 C ⇌32/58 X

MDW523   I ⇌101 N ⇌91 C ⇌18/60 X

TABLE 1-continued

Phase Properties of Representative Compounds of this Invention.

MDW555   I ⇌110 C ⇌95/97 X

MDW556   I ⇌89 N ⇌74 C ⇌42/51 X

MDW565   I ⇌76 N ⇌52 C ⇌51/72 X

MDW569   I ⇌98 $S_B$ ⇌<RT X

MDW571   I ⇌123 $S_B$ ⇌<RT X

MDW576   I ⇌107 N ⇌68 C ⇌45/54 $S_x$ ⇌35/50 X

MDW577   I ⇌142 N ⇌121 A ⟶117 C ⟶45 $S_x$ ⟶ X

MDW578   I ⇌138 N ⇌112 C ⇌63/82 X

MDW579   I ⇌127 N ⇌108 C ⇌64/95 X

MDW580   I ⇌124 N ⇌118 C ⇌72/86 X

MDW583   I ⇌146 N ⇌60/73 X

MDW588   I ⇌119 N ⇌106 C ⇌/98 X

MDW589   I ⇌97 N ⇌76 C ⇌60/82 X

MDW590   I ⇌129 N ⇌118 A ⇌73 C ⇌64/111 X

TABLE 2

| ID# | Structure of dopant 20% w/w in MX5343  10% w/w MDW232 | Melting Point (°C.) | Super-cooling (°C.) | C* pitch (μm) | Tilt Angle (°) | Rise Time (μs @ 5 V/μm) |
|---|---|---|---|---|---|---|
| set A | | | | | | |
| MDW337 | [pentyl-cyclohexyl-C(=O)O-phenyl-pyrimidine-C10H21] | 5 | 7 | −0.9/−2.4* | 25/28* | 77 |
| MDW336 | [prenyl-cyclohexene-C(=O)O-phenyl-pyrimidine-C10H21] | 0 | −9 | −1.3/−3.3* | 21/21* | 63 |
| set B | | | | | | |
| MDW342 | [pentyl-cyclohexyl-CH2-O-phenyl-pyrimidine-C9H19] | 9 | −7 | −1.2 | 25 | 97 |
| MDW343 | [prenyl-cyclohexene-CH2-O-phenyl-pyrimidine-C9H19] | 1 | −10 | −1.6 | 21 | 60 |
| set C | | | | | | |
| MDW489 | [pentyl-cyclohexyl-C(=O)O-phenyl-pyridine-C8H17] | 3 | −15 | −1.5 | 26 | 134 |

TABLE 2-continued
| ID# | Structure of dopant 20% w/w in MX5343 10% w/w MDW232 | Melting Point (°C.) | Super-cooling (°C.) | C* pitch (μm) | Tilt Angle (°) | Rise Time (μs @ 5 V/μm) |
|---|---|---|---|---|---|---|
| MDW588 | 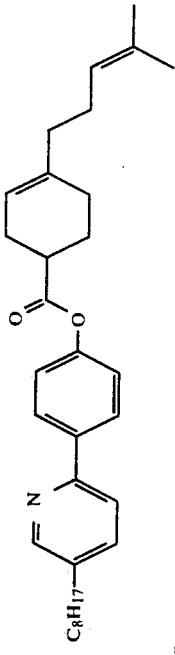 | 1 | −19 | −1.8 | 23 | 80 |
*5% w/w MDW232

TABLE 3

| ID# | Phase diagrams of 20% cyclohexenyl dopant in smectic C host MX5343 |
|---|---|
| MX5343 (reference) Table 3 | I ←70→ N ←66→ A ←47→ C −5/−7 Sx −1 X |
| MDW336 | I ←77→ N ←69→ A ←58→ C −8/−6 Sx −3 X |
| MDW343 | I ←78→ N ←70→ A ←57→ C 0/4 X |
| MDW555 | I ←77→ N ←74→ A ←63→ C −13/0 Sx −6 X |
| MDW576 | I ←75→ N ←68→ A ←57→ C −7/3 X |
| MDW577 | I ←81→ N ←70→ A ←62→ C −19/2 Sx −2 X |
| MDW578 | I ←81→ N ←73→ A ←61→ C −11/1 X |
| MDW579 | I ←81→ N ←78→ A ←57→ C −17/8 Sx −18/−1 X |
| MDW580 | I ←81→ N ←75→ A ←62→ C −9/6 Sx 1 X |

TABLE 4

The compositions of MX5343 and MX6111 are as follows:

| Short name | Structure | MX5434 (% w/w) | MX6111 (% w/w) |
|---|---|---|---|
| 7O6 | 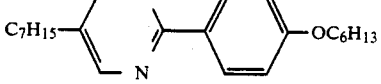 C$_7$H$_{15}$-[pyrimidine]-[phenyl]-OC$_6$H$_{13}$ | 7.0 | 5.6 |
| 7O7 |  C$_7$H$_{15}$-[pyrimidine]-[phenyl]-OC$_7$H$_{15}$ | 7.0 | 5.6 |
| 7O8 |  C$_7$H$_{15}$-[pyrimidine]-[phenyl]-OC$_8$H$_{17}$ | 7.0 | 5.6 |
| 7O9 | 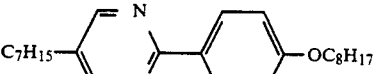 C$_7$H$_{15}$-[pyrimidine]-[phenyl]-OC$_9$H$_{19}$ | 9.0 | 7.2 |
| 9O6 | 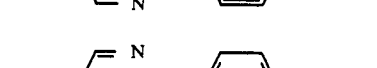 C$_9$H$_{19}$-[pyrimidine]-[phenyl]-OC$_6$H$_{13}$ | 12.0 | 9.6 |
| 9O7 | 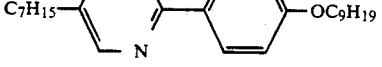 C$_9$H$_{19}$-[pyrimidine]-[phenyl]-OC$_7$H$_{15}$ | 9.0 | 7.2 |

TABLE 4-continued

The compositions of MX5343 and MX6111 are as follows:

| Short name | Structure | MX5434 (% w/w) | MX6111 (% w/w) |
|---|---|---|---|
| 908 | C$_9$H$_{19}$—[pyrimidine]—[phenyl]—OC$_8$H$_{17}$ | 7.0 | 5.6 |
| 909 | C$_9$H$_{19}$—[pyrimidine]—[phenyl]—OC$_9$H$_{19}$ | 42.0 | 33.6 |
| 900H | C$_9$H$_{19}$—[pyrimidine]—[phenyl]—O—CH$_2$—[cyclohexyl]—CH=CH—CH$_2$—CH$_3$ | 0 | 20 |

We claim:

1. A compound of the formula:

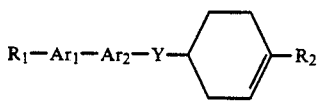

wherein R$_1$ and R$_2$, independently of one another, are selected from the group consisting of alkyl, cycloalkyl, alkenyl, alkoxy, thioalkyl and alkylsilyl, groups having from 1-20 carbon atoms; Y can be —CH$_2$O—, —COO—, —OOC— or —OCH$_2$—; and Ar$_1$ and Ar$_2$, independently of one another, are selected from the group consisting of 1,4-phenyl, mono- or difluorinated 1,4-phenyl, 2,5-pyridinyl, 2,5-pyrimidyl, 2,5-pyrazinyl, 2,5-thiadiazole, 3,6-pyridazinyl and trans-1,4-cyclohexyl wherein at least one of Ar$_1$ or Ar$_2$ is a nitrogen-containing aromatic ring.

2. A compound according to claim 1 wherein Y is —O—CH$_2$— or —CH$_2$—O—.

3. A compound according to claim 2 wherein one of Ar$_1$ or Ar$_2$ is a 2,5-substituted pyrimidine.

4. A compound according to claim 3 wherein one of Ar$_1$ or Ar$_2$ is a 2,5-substituted pyridine.

5. A compound according to claim 2 wherein one of Ar$_1$ or Ar$_2$ is a 2,3-difluoro-1,4-substituted phenyl, a 2-fluoro-1,4-substituted phenyl or a 3-fluoro-1,4-substituted phenyl.

6. A compound according to claim 2 wherein one of Ar$_1$ or Ar$_2$ is a trans-1,4-cyclohexane.

7. A compound according to claim 2 wherein R$_1$ and R$_2$, independently of one another, are selected from the group consisting of alkyl, alkenyl, alkoxy and thioalkyl groups.

8. A compound according to claim 2 wherein R$_2$ and R$_2$, independently of one another, are alkyl or alkene groups.

9. A compound according to claim 8 wherein R$_1$ and R$_2$ contain five to twelve carbon atoms.

10. A compound according to claim 1 wherein Y is —OOC— or —COO—.

11. A compound according to claim 10 wherein one of Ar$_1$ or Ar$_2$ is a 2,5-substituted pyrimidine.

12. A compound according to claim 10 wherein one of Ar$_1$ or Ar$_2$ is a 2,5-substituted pyridine.

13. A compound according to claim 10 wherein one of Ar$_1$ and Ar$_2$ is a 2,3-difluorine, 1,4-substituted phenyl, a 2-fluoro-1,4-substituted phenyl or a 3-fluoro-1,4-substituted phenyl.

14. A compound according to claim 10 wherein one of Ar$_1$ or Ar$_2$ is a trans-1,4-cyclohexane.

15. A compound according to claim 10 wherein R$_1$ and R$_2$, independently of one another, are selected from the group consisting of alkyl, alkenyl, alkoxy and thioalkyl groups.

16. A compound according to claim 10 wherein R$_1$ and R$_2$, independently of one another, are alkyl or alkene groups.

17. A compound according to claim 10 wherein R$_1$ and R$_2$ contain five to twelve carbon atoms.

18. A ferroelectric liquid crystal composition comprising one or more of the compounds of claim 1.

19. A ferroelectric liquid crystal composition comprising one or more of the compounds of claim 2.

20. A ferroelectric liquid crystal composition comprising one or more of the compounds of claim 10.

21. A compound according to claim 1 wherein Y is —OCH$_2$—.

22. A compound according to claim 21 wherein R$_1$ and R$_2$, independently of one another, are selected from the group consisting of alkyl, alkenyl, alkoxy and thioalkyl groups.

23. A compound according to claim 21 wherein R$_1$ and R$_2$, independently of one another, are alkyl or alkenyl groups.

24. A ferroelectric liquid crystal composition comprising one or more of the compounds of claim 21.

25. A compound according to claim 1 wherein Y is —OOC—.

26. A compound according to claim 25 wherein R$_1$ and R$_2$, independently of one another, are selected from the group consisting of alkyl, alkenyl, alkoxy and thioalkyl groups.

27. A compound according to claim 25 wherein R$_1$ and R$_2$, independently of one another, are alkyl or alkenyl groups.

28. A ferroelectric liquid crystal composition comprising one or more of the compounds of claim 25.

* * * * *